(12) United States Patent
Van Dijk et al.

(10) Patent No.: US 8,012,733 B2
(45) Date of Patent: Sep. 6, 2011

(54) SIALIDASES

(75) Inventors: Albertus Alard Van Dijk, Vlaardingen (NL); Natalja Alekseevna Cyplenkova, legal representative, Vlaardingen (NL); Petrus Jacobus Theodorus Dekker, Den Haag (NL); Yulia M. Efimova, Delft (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/527,064

(22) PCT Filed: Feb. 18, 2008

(86) PCT No.: PCT/EP2008/051930
§ 371 (c)(1),
(2), (4) Date: Jan. 21, 2010

(87) PCT Pub. No.: WO2008/101893
PCT Pub. Date: Aug. 28, 2008

(65) Prior Publication Data
US 2010/0167344 A1      Jul. 1, 2010

(30) Foreign Application Priority Data
Feb. 20, 2007   (EP) .................................... 07102688

(51) Int. Cl.
C12N 9/24     (2006.01)
C12N 15/56    (2006.01)
C12N 15/74    (2006.01)
C12N 15/79    (2006.01)
C12N 15/80    (2006.01)
A23C 19/032   (2006.01)
A23K 1/165    (2006.01)

(52) U.S. Cl. ..................... 435/200; 435/69.1; 435/252.3; 435/254.11; 435/320.1; 536/23.2; 426/42; 426/53

(58) Field of Classification Search ........................ None
See application file for complete search history.

(56) References Cited

U.S. PATENT DOCUMENTS

| | | | | | |
|---|---|---|---|---|---|
| 4,925,680 | A | * | 5/1990 | Schweikhardt et al. | 426/42 |
| 5,928,915 | A | * | 7/1999 | Warner et al. | 435/455 |
| 7,645,448 | B2 | * | 1/2010 | Fang et al. | 424/94.6 |
| 7,807,174 | B2 | * | 10/2010 | Fang et al. | 424/192.1 |
| 2007/0031397 | A1 | * | 2/2007 | Schnaar et al. | 424/94.61 |
| 2010/0196539 | A1 | * | 8/2010 | Van Dijk et al. | 426/64 |

OTHER PUBLICATIONS

Christiansen et al. "Cloning, expression and characterization of a sialidase gene from *Arthrobacter ureafaciens*" *Biotechnology and Applied Biochemistry*, vol. 41, No. 1, pp. 225-231, (Jun. 2005).
Database Sptrembl "Extracellular sialidase/neuraminidase, putative (EC 3.2.1.18)" EMBL Accession Q4WM08, one page (Jul. 5, 2005).
Nierman et al. "Genomic sequence of the pathogenic and allergenic filamentous fungus *Aspergillus fumigatus*" UNIPROT Accession Q4WQS0, one page (Jul. 5, 2005).

(Continued)

*Primary Examiner* — Nashaat Nashed
*Assistant Examiner* — William W Moore
(74) *Attorney, Agent, or Firm* — Nixon & Vanderhye

(57) ABSTRACT

Isolated polypeptide having sialidase activity and having an amino acid sequence which has at least 90% amino acid sequence identity with amino acids 34 to 407 of SEQ ID NO: 3.

20 Claims, 1 Drawing Sheet

OTHER PUBLICATIONS

Figure 1:
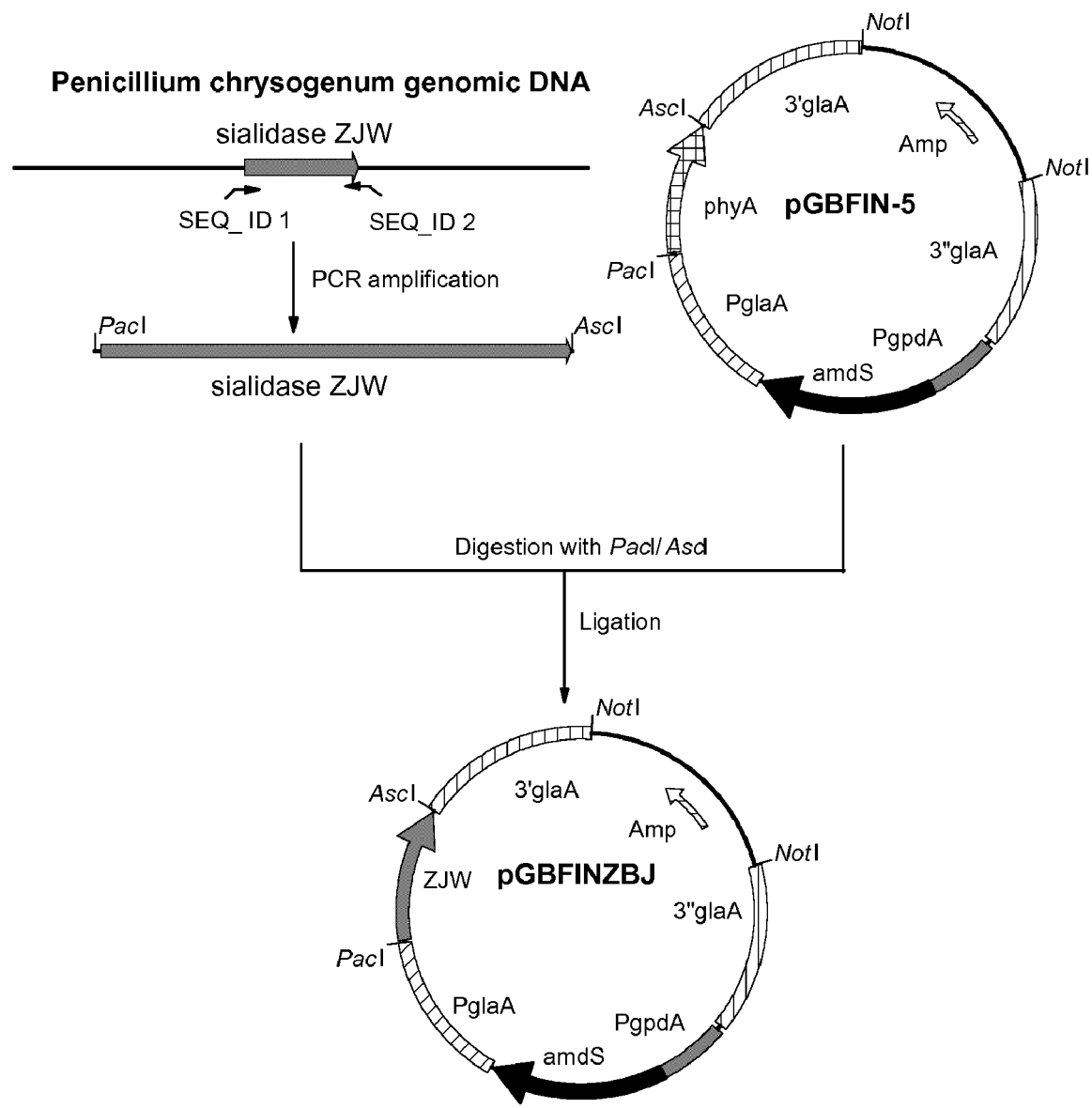

Schmidt et al. "Structure of the xylanase from *Penicilium simplicissiumum*" Protein Science, vol. 7, No. 10, pp. 2081-2088 (Oct. 1998).

Uchida et al. "Production of microbial neuraminidases EC-3.2.1.18 induced by colominic-acid" Biochimica et Biophysica Acta, vol. 350, No. 2, pp. 425-431 (Jan. 1974).

* cited by examiner

SIALIDASES

This application is the U.S. national phase under 35 U.S.C. 371 of International Application No. PCT/EP2008/051930, filed 18 Feb. 2008, which designated the U.S. and claims priority to Application No. EP 07102688.4 filed 20 Feb. 2007; the entire contents of which are hereby incorporated by reference.

FIELD OF THE INVENTION

The invention relates to a novel sialidase.

BACKGROUND OF THE INVENTION

Sialic acids comprise a family of about 40 derivatives of the nine-carbon sugar neuraminic acid. It is a strong organic acid with a $pK_a$ of around 2.2. The unsubstituted form, neuraminic acid, does not exist in nature. The amino group is usually acetylated to yield N-acetylneuraminic acid, the most widespread form of sialic acid, but other forms exist as well (Traving et al Cell Mol Life Sci (1998) 54, 1330-1349). Sialic acids have been found in the animal kingdom, from the echinoderms upwards to humans whereas there is no hint for their existence in lower animals of the protostomate lineage or in plants. The only known exception is the occurrence of polysialic acid in larvae of the insect *Drosophila*. In addition there are sialic acids in some protozoa, viruses and bacteria. Sialoglycoconjugates are present on cell surfaces as well as in intracellular membranes. In higher animals they are also important components of the serum and of mucous substances.

Sialic acids have a variety of biological functions. Due to their negative charge sialic acids are involved in binding and transport of positively charged molecules like calcium ions, as well as in attraction and repulsion phenomena between cells and molecules. Their exposed terminal position in carbohydrate chains, in addition to their size and negative charge enable them to function as a protective shield for the subterminal part of the molecule or the cell. They can e.g. prevent glycol-proteins from being degraded by proteases or the mucous layer of the respiratory system from bacterial infection. An interesting phenomenon is the spreading effect that is exerted on sialic acid containing molecules due to the repulsive forces acting between their negative charges. This stabilizes the correct conformation of enzyme or membrane (glyco)-proteins, and is important for the slimy character and the resulting gliding and protective function of mucous substances, such as on the surface to the eye or on mucous epithelia (Traving et al Cell Mol Life Sci (1998) 54, 1330-1349). Clearly, treatment of such sialic acid containing substances with a suitable sialidase can dramatically affect the biological properties and physical characteristics of such substances. Treatment of sialic acid containing proteins with a sialidase can make them much easier to degrade by proteases, treatment of mucous substances with sialidase could strongly reduce or eliminate their slimy characteristics. Such changes would be interesting in case such proteins need processing (e.g. proteolysis) industrial processes for e.g. protein hydrolysates.

Sialic acids take part in a variety of recognition processes between cells and molecules. Thus, the immune system can distinguish between self and non-self structures according to their sialic acid pattern. The sugar represents an antigenic determinant, for example blood group substances, and is a necessary component of receptors for many endogenous substances such as hormones and cytokines. In addition, many pathogenic agents such as toxins (e.g. cholera toxin), viruses (e.g. influenza) bacteria (e.g. *Escherichia coli, Helicobacter pylori*) and protozoa (e.g. *Trypanosome cruzi*) also bind host cells via sialic acid-containing receptors. Another important group of sialic acid recognizing molecules belong to the lectins, which are usually oligomeric glycoproteins from plants, animals and invertebrates that bind specific sugar residues. Examples are wheat germ agglutinin, *Limulus polyphemus* agglutinin, *Sambucus nigra* agglutinin and *Maackia amurensis* agglutinin. These lectins seem to help the plant in its defense against sialic acid containing micro-organisms or plant-eating mammals. Mammalian counterparts of the lectins include selectins and siglecs (Traving et al Cell Mol Life Sci (1998) 54, 1330-1349) and have a variety of physiological roles. Sialic acids can also assist in masking of cells and molecules. Erythrocytes are covered by a dense layer of sialic acid molecules, which is stepwise removed during the life cycle of the blood cell. The penultimate galactose residue that represent signals for degradation than become visible and the unmasked blood cells are than bound to macrophages and phagocytosed. Several other examples of such masking strategy are known. Masking can also have a detrimental effect, as can be seen from some of the tumors that are sialylated to a much higher degree than the corresponding tissues. Consequently, the masked cells are invisible to the immune defense system, and the high sialic acid contents may also play a role in the lack of inhibition of further cell growth and in spreading. The masking effect of sialic acids also helps to hide antigenic sites on parasite cells, making them invisible for the system. This is the case for microbial species like certain *E coli* strains and gonococci (*Neisseria gonorrhoea*). Treatment of such species with a sialidase would affect their possibilities to hide from the immune system.

Sialidases (neuraminidases, EC 3.2.1.18) hydrolyze the terminal, non-reducing, sialic acid linkage in glycoproteins, glycolipids, gangliosides, polysaccharides and synthetic molecules. Some sialidases, called transsialidases, are also capable to perform transfer-reactions in which they transfer the sialic acid residue from one molecule to another. Sialidases are common in animals of the deuterostomate lineage (Echinodermata through Mammalia) and also in diverse microorganisms that mostly exist as animal commensals or pathogens. Sialidases, and their sialyl substrates, appear to be absent from plants and most other metazoans. Even among bacteria, sialidase is found irregularly so that related species or even strains of one species differ in this property. Sialidases have also been found in viruses and protozoa (Traving et al Cell Mol Life Sci (1998) 54, 1330-1349). Micro-organisms containing sialidases often live in contact with higher animals as hosts, for example as parasites. Here they may have a nutritional function enabling their owners to scavenge host sialic acids to use as a carbon source. For some microbial pathogens, sialidases are believed to act as virulence factors. Yet, the role of salidases as factors in pathogenesis is controversial. On the one hand they confirm the impact of pathogenic microbial species like *Clostridium perfringens*. On the other hand, these enzymes are factors common in the carbohydrate catabolism of many non-pathogenic species, including higher animals. They do not, however, exert a direct toxic effect (Traving et al Cell Mol Life Sci (1998) 54, 1330-1349). Instead, their detrimental effect depends on the massive amount of enzyme that is released into the host together with other toxic factors upon induction by host sialic acids under non-physiological conditions.

The mammalian sialidases are normally approximately 40-45 kDa in size. Attempts to over-express and produce mammalian sialidases to industrially interesting amounts have not been reported. Human sialidases can be lysosomal, cytosolic or membrane bound enzymes (Achyuthan and Achyuthan (2001) Comp. Biochem. Phys. Part B, 129, 29-64). The lysosomal sialidases are glycosylated enzymes. Sialidases contain conserved motifs. The most prominent conserved motif is the so-called Asp-box, which is a stretch of amino acids of the general formula -S-X-D-X-G-X-T-W- where X represents a variable residue. This motif is found four to five times throughout all microbial sequences with the exception of viral sialidases, where it is found only once or twice or is even absent. The third Asp-box is more strongly conserved than are Asp-boxes 2 and 4. The space between two sequential Asp-boxes is also conserved between different primary structures (Traving et al Cell Mol Life Sci (1998) 54, 1330-1349). The Asp-boxes probably have a structural role and are probably not involved in catalysis. In contrast to the Asp-boxes, the FRIP-motif is located in the N-terminal part of the amino acid sequences. It encompasses the amino acids -X-R-X-P- with the arginine and praline residues absolutely conserved. The arginine is directly involved in catalysis by binding of the substrate molecule. Also important for catalytic action is a glutamic acid rich region between asp-boxes 3 and 4 as well as two further arginine residues (Traving et al Cell Mol Life Sci (1998) 54, 1330-1349)

Microbial sialidases can be classified into two groups according to their size: small proteins of around 42 kDa and large ones of 60-70 kDa. The primary structure of the large sialidases contain extra stretches of amino acids between the N-terminus and the second Asp-box as well as between the fifth Asp-box and the C-terminus. It is believed that they contribute to the broader substrate specificity of the large sialidases. Like the mammalian sialidases, the bacterial counterparts contain the F/YRIP motif and several Asp-boxes. Bacterial sialidases are often implicated in mucosal infections and virulence. Because of this, the larger bacterial sialidases are not regarded suitable for the use as processing aid in food or pharma applications. Small sialidases (same size as the mammalian sialidases) have been identified in bacteria, as indicated above. I.e. *Clostridium perfringens* contains a small sialidase with a size of ~40 kDa, without the extensions common to sialidases in other bacteria. This *Clostridium* sialidase is however not secreted by the bacterium, and is therefore also not involved in virulence (Roggentin et al. (1995) Biol Chem Hoppe Seyler 376, 569-575). It is tempting to speculate that only the bacterial sialidases with extra extensions are involved in pathogenicity. Overexpression of bacterial sialidases in *E. coli* generally leads to low productivity; the small *Clostridium* sialidase could only be produced to 1 mg/l as intracellular protein in *E. coli* (Kruse et al. (1996) Protein Expr Purif. 7, 415-422).

Uchida et al (Biochimica et Biophysica Acta, vol. 350, no. 2, 1974 pp 425-431) describe the screening of microbial neuraminidases which are induced by colominic acid. Among 1000 microorganisms screened, neuramidases were obtained from *Sporotrichium schenckii*, *Penicillium urticae* and *Streptomyces* sp. were obtained. *Penicillium urticae* is not a suitable production organism for food-grade sialidase, since it is a fungus involved in food spoilage, and *Sporotrichium schenckii* is a pathogenic fungus. Of the bacterium *Streptomyces* sp the species name is not determined. The MW of the sialidases mentioned in this article is unknown. In Iwamori et al (J. Biochem. 138, pp 327-334) a bacterial *Arthrobacter ureafaciens* sialidases is disclosed. However this bacterial neuramidase is known to be related in HIV-1 Mediated Syncytium Formation and the Virus Binding/Entry Process (Sun et al, Virology 284, pp 26-36, 2001). There is therefore a clear need for a well-produced small, non-virulent sialidase for applications in food and pharma.

Especially the finding of a secreted fungal sialidase would be beneficial, since secreted enzymes can be easily overexpressed and purified in large quantities from a fungal culture. This would reduce the cost-price for production of a sialidase dramatically.

SUMMARY OF THE INVENTION

The present invention relates to an isolated polypeptide which has sialidase activity, selected from the group consisting of:
(a) a polypeptide which has an amino acid sequence which has at least 60% amino acid sequence identity with amino acids 1 to 407 of SEQ ID NO:3;
(b) a polypeptide which is encoded by a polynucleotide which hybridizes under low stringency conditions with (i) the nucleic acid sequence of SEQ ID NO: 1 or 2 which is at least 80% or 90% identical over 60, preferably over 100 nucleotides, more preferably at least 90% identical over 200 nucleotides, or (ii) a nucleic acid sequence complementary to the nucleic acid sequence of SEQ ID NO: 1 or 2. Preferably the polypeptide has MW (molecular weight) of less than 55 kD (SDS-page), more preferably the polypeptide has MW (molecular weight) of less than 52 kD (SDS-page) or the polypeptide has a MW (molecular weight) of less than 50 kDa (calculated on basis of amino acid sequence), more preferably the polypeptide has MW (molecular weight) of less than 45 kDa (calculated on basis of amino acid sequence).

Moreover the present invention provides a polypeptide having sialidase activity and which is non-virulent. Also part of the present invention is a polypeptide having sialidase activity, said polypeptide is a fungal sialidase which has a MW (molecular weight) of less than 55 kDa (SDS-page), more preferably the fungal sialidase has a MW (molecular weight) of less than 52 kDa (SDS-page) or the fungal sialidase has a MW (molecular weight) of less than 50 kDa (calculated on basis of amino acid sequence), more preferably the fungal sialidase has a MW (molecular weight) of less than 45 kDa (calculated on basis of amino acid sequence).

Preferably the polypeptide of the invention which has an amino acid sequence which has at least 65%, preferably at least 70%, more preferably at least 80%, even more preferably at least 90%, most preferably at least 95%, and even most preferably at least about 97% identity with amino acids 1 to 407 of SEQ ID NO: 3. The present invention also relates to an isolated polynucleotide comprising a nucleic acid sequence which encodes the polypeptide of claim 1, or which hybridizes with SEQ ID NO: 1 or 2 under low stringency conditions, more preferably medium stringency conditions, and most preferably high stringency conditions. Furthermore, the present invention discloses a nucleic acid construct comprising the polynucleotide of the invention operably linked to one or more control sequences that direct the production of the polypeptide in a suitable expression host. Moreover the present invention provides a recombinant expression vector comprising this nucleic acid construct and a recombinant host cell comprising said nucleic acid construct. According to another aspect of the invention a method for producing the polypeptide of the invention is disclosed comprising cultivating a strain/recombinant host cell as mentioned above, to produce a supernatant and/or cells comprising the polypeptide; and recovering the polypeptide. According to a further aspect of the invention a method for producing the polypeptide of the invention is disclosed comprising cultivating a host cell comprising a nucleic acid construct comprising a polynucleotide encoding the polypeptide under conditions suitable for production of the polypeptide; and recovering the polypeptide. The polypeptide of the invention having sialidase activity is advantageously non-virulent. The polypeptide of the invention can be used in the preparation of food or feed, or as a medicament or part of a medicament.

DETAILED DESCRIPTION OF THE INVENTION

According to the present invention a small-sized sialidase is disclosed that has preferably having a MW (molecular weight) of less than 55 kDa (SDS-page), more preferably the polypeptide has MW (molecular weight) of less than 52 kDa (SDS-page) or a sialidase which has a MW (molecular weight) of less than 50 kDa (calculated on basis of amino acid sequence), more preferably the polypeptide has MW (molecular weight) of less than 45 kDa (calculated on basis of amino acid sequence). Advantageously the sialidase of the invention an extracellular enzyme. Moreover the sialidase is preferably of a fungal origin. In general, the polypeptide of the invention will have a MW (molecular weight) of more than 35 kDa (SDS-page), more preferably the polypeptide has MW (molecular weight) of more than 40 kDa (SDS-page) or the polypeptide will have a MW (molecular weight) of more than 35 kDa (calculated on basis of amino acid sequence), more preferably the polypeptide has a MW (molecular weight) of more than 40 kDa (calculated on basis of amino acid sequence).

An exoenzyme, or extracellular enzyme, is an enzyme that is secreted by a cell and that works outside that cell. It is usually used for breaking up large molecules that would not be able to enter the cell otherwise. It is an enzyme that organisms secrete into the environment which acts outside the microbe. The opposite of an exoenzyme is called an endoenzyme or intracellular enzyme (source is Wikipedia)

It is the theory of the present inventors that in general large sialidases relate to mucosal infections and virulence and are therefore not suitable in food or pharma applications. In contrast thereto small sialidases are believed to suitable for food or pharma applications.

However the present invention does not stand or fall with the correctness of this theory. The present invention provides an extracellular sialidase having a has a MW (molecular weight) of less than 55 kDa (SDS-page), more preferably the sialidase has MW (molecular weight) of less than 52 kDa (SDS-page) or an extracellular sialidase which has a MW (molecular weight) of less than 50 kDa (calculated on basis of amino acid sequence), more preferably the sialidase has MW (molecular weight) of less than 45 kDa (calculated on basis of amino acid sequence)

The present invention relates to a new sialidase which has been identified in the fungus *Penicillium chrysogenum.*

Advantageously the present invention meets the demand for a sialidase that can be produced in high amounts. Preferably, such a sialidase is secreted from the host cell. Active secretion is of paramount importance for an economical production process because it enables the recovery of the enzyme in an almost pure form without going through cumbersome purification processes. Overexpression of such an actively secreted sialidase by a food grade fungal host such as *Aspergillus*, yields a food grade enzyme and a cost effective production process, and is therefore preferable. The presently secreted sialidase is for the first time found in filamentous fungi. Processes are disclosed for the production of sialidase in large amounts by the food-grade production host *Aspergillus niger.*

From an economic point of view there exists a clear need for an improved means of producing sialidases in high quantities and in a relatively pure form, compared to the poor productivity of the mammalian and bacterial sialidases. A preferred way of doing this is via the overproduction of such a sialidase using recombinant DNA techniques. A particularly preferred way of doing this is via the overproduction of a fungal derived sialidase and a most preferred way of doing this is via the overproduction of an *Penicillium* derived sialidase. To enable the latter production route unique sequence information of an *Penicillium* derived sialidase is essential. More preferable the whole nucleotide sequence of the encoding gene has to be available.

An improved means of producing the newly identified secreted sialidase in high quantities and a relatively pure form is via the overproduction of the *Penicillium* encoded enzyme using recombinant DNA techniques. A preferred way of doing this is via the overproduction of such a secreted sialidase in a food grade host microorganism. Well known food grade microorganisms include Aspergilli, *Trichoderma, Streptomyces*, Bacilli and yeasts such as *Saccharomyces* and *Kluyveromyces*. An even more preferred way of doing this is via overproduction of the secreted *Penicillium* derived sialidase in a food grade fungus such as *Aspergillus*. Most preferred is the over production of the secreted sialidase in a food grade fungus in which the codon-usage of the sialidase-encoding gene has been optimized for the food grade expression host used. In general, to enable the latter optimization routes, unique sequence information of a secreted sialidase is desirable. More preferable the whole nucleotide sequence of the sialidase encoding gene has to be available. Once the gene encoding a secreted sialidase is transformed in a preferred host, selected strains can be used for fermentation and isolation of the secreted sialidase protein from the fermentation broth.

Once the new enzyme has been made available in large quantities and in a relatively pure food, food stuffs (like cheese), protein hydrolysates with improved textural and/or immunological properties can be prepared in a food grade and economic way. The enzyme can also potentially be used as a preservative. By removing the protective sialic acid residues from the bacterial walls, the microbes will be recognized by the immune system and eliminated.

A polypeptide of the invention which has sialidase activity may be in an isolated form. As defined herein, an isolated polypeptide is an endogenously produced or a recombinant polypeptide which is essentially free from other non-sialidase polypeptides, and is typically at least about 20% pure, preferably at least about 40% pure, more preferably at least about 60% pure, even more preferably at least about 80% pure, still more preferably about 90% pure, and most preferably about 95% pure, as determined by SDS-PAGE. The polypeptide may be isolated by centrifugation and chromatographic methods, or any other technique known in the art for obtaining pure proteins from crude solutions. It will be understood that the polypeptide may be mixed with carriers or diluents which do not interfere with the intended purpose of the polypeptide, and thus the polypeptide in this form will still be regarded as isolated. It will generally comprise the polypeptide in a preparation in which more than 20%, for example more than 30%, 40%, 50%, 80%, 90%, 95% or 99%, by weight of the proteins in the preparation is a polypeptide of the invention.

Preferably, the polypeptide of the invention is obtainable from a microorganism which possesses a gene encoding an enzyme with sialidase activity. More preferably polypeptide of the invention is secreted from a microorganism. Even more preferably the microorganism is fungal, and optimally is a filamentous fungus. Preferred donor organisms are thus of the genus *Penicillium*, such as those of the species *Penicillium chrysogenum*. In a first embodiment, the present invention provides an isolated polypeptide having an amino acid sequence which has a degree of amino acid sequence identity to amino acids 1 to 407 of SEQ ID NO:3 (i.e. the polypeptide) of at least 60%, preferably at least 70%, more preferably at least 80%, even more preferably at least 90%, still more preferably at least 95%, and most preferably at least 97%, and which has sialidase activity.

For the purposes of the present invention, the degree of identity between two or more amino acid sequences is determined by BLAST P protein database search program (Altschul et al., 1997, Nucleic Acids Research 25: 3389-3402) with matrix Blosum 62 and an expected threshold of 10.

A polypeptide of the invention may comprise the amino acid sequence set forth in SEQ ID NO:3 or a substantially homologous sequence, or a fragment of either sequence having sialidase activity. In general, the naturally occurring amino acid sequence shown in SEQ ID NO: 3 is preferred.

One aspect of the invention is a polypeptide having amino acid sequence shown in SEQ ID NO: 3 whereby signal sequence is removed. Secreted enzymes, like the amino acid sequence of SEQ ID NO: 3, are often synthesized including a pre- or signal-sequence and/or a pro-sequence. These sequences are often removed from the protein either during or after the secretion process. The mature secreted protein therefore often does not contain these pre- and pro-sequences anymore. Therefore a polypeptide which has an amino acid sequence which has at least 60% amino acid sequence identity with amino acids 1 to 407 of SEQ ID NO: 3 and lacking possible pre- or pro-sequences is part of the present invention. A possible processing site in the amino acid sequence of SEQ ID NO: 3 is after amino acid 33. The mature enzyme according to the invention will in this case start at amino acid number 34. Other modifications from the amino acid sequence of SEQ ID NO: 3 due to further processing, such as removal of amino acids, are allowed as long that they do not disturb the activity of the enzyme.

The polypeptide of the invention may also comprise a naturally occurring variant or species homologue of the polypeptide of SEQ ID NO: 3.

A variant is a polypeptide that occurs naturally in, for example, fungal, bacterial, yeast or plant cells, the variant having sialidase activity and a sequence substantially similar to the protein of SEQ ID NO: 3. The term "variants" refers to polypeptides which have the same essential character or basic biological functionality as the sialidase of SEQ ID NO: 3, and includes allelic variants. Preferably, a variant polypeptide has at least the same level of sialidase activity as the polypeptide of SEQ ID NO: 3. Variants include allelic variants either from the same strain as the polypeptide of SEQ ID NO: 3 or from a different strain of the same genus or species.

Similarly, a species homologue of the inventive protein is an equivalent protein of similar sequence which is a sialidase and occurs naturally in another species.

Variants and species homologues can be isolated using the procedures described herein and performing such procedures on a suitable cell source, for example a bacterial, yeast, fungal or plant cell. Also possible is to use a probe of the invention to probe DNA libraries made from yeast, bacterial, fungal or plant cells in order to obtain clones expressing variants or species homologues of the polypeptide of SEQ ID NO:3. The methods that can be used to isolate variants and species homologues of a known gene are extensively described in literature, and known to those skilled in the art. These genes can be manipulated by conventional techniques to generate a polypeptide of the invention which thereafter may be produced by recombinant or synthetic techniques known per se.

The sequence of the polypeptide of SEQ ID NO: 3 and of variants and species homologues can also be modified to provide polypeptides of the invention. Amino acid substitutions may be made, for example from 1, 2 or 3 to 10, 20 or 30 substitutions. The same number of deletions and insertions may also be made. These changes may be made outside regions critical to the function of the polypeptide, as such a modified polypeptide will retain its sialidase activity.

Polypeptides of the invention include fragments of the above mentioned full length polypeptides and of variants thereof, including fragments of the sequence set out in SEQ ID NO: 3. Such fragments will typically retain activity as an sialidase. Fragments may be at least 50, 100 or 200 amino acids long or may be this number of amino acids short of the full length sequence shown in SEQ ID NO: 3.

Polypeptides of the invention can, if necessary, be produced by synthetic means although usually they will be made recombinantly as described below. Synthetic and recombinant polypeptides may be modified, for example, by the addition of histidine residues or a T7 tag to assist their identification or purification, or by the addition of a signal sequence to promote their secretion from a cell.

Thus, the variants sequences may comprise those derived from strains of *Penicillium* other than the strain from which the polypeptide of SEQ ID NO:3 was isolated. Variants can be identified from other *Penicillium* strains by looking for sialidase activity and cloning and sequencing as described herein. Variants may include the deletion, modification or addition of single amino acids or groups of amino acids within the protein sequence, as long as the peptide maintains the basic biological functionality of the sialidase of SEQ ID NO: 3

Amino acid substitutions may be made, for example from 1, 2 or from 3 to 10, 20 or 30 substitutions. The modified polypeptide will generally retain activity as a sialidase. Conservative substitutions may be made; such substitutions are well known in the art.

Shorter or longer polypeptide sequences are within the scope of the invention. For example, a peptide of at least 50 amino acids or up 100, 150, 200, 300, 400, 500, 600, 700 or 800 amino acids in length is considered to fall within the scope of the invention as long as it demonstrates the basic biological functionality of the sialidase of SEQ ID NO:3. In particular, but not exclusively, this aspect of the invention encompasses the situation in which the protein is a fragment of the complete protein sequence.

The present invention also relates to a polynucleotide which encodes a polypeptide which has sialidase activity, said polynucleotide comprises a polynucleotide sequence which encodes amino acid SEQ ID NO: 3.

For the present invention it is especially relevant that the protein of interest is actively secreted into the growth medium. Secreted proteins are normally originally synthesized as pre-proteins and the pre-sequence (signal sequence) is subsequently removed during the secretion process. The secretion process is basically similar in prokaryotes and eukaryotes: the actively secreted pre-protein is threaded through a membrane, the signal sequence is removed by a specific signal peptidase, and the mature protein is (re)-folded. Also for the signal sequence a general structure can be recognized. Signal sequences for secretion are located at the amino-terminus of the pre-protein, and are generally 15-35 amino-acids in length. The amino-terminus preferably contains positively charged amino-acids, and preferably no acidic amino-acids. It is thought that this positively charged region interacts with the negatively charged head groups of the phospholipids of the membrane. This region is followed by a hydrophobic, membrane-spanning core region. This region is generally 10-20 amino-acids in length and consists mainly of hydrophobic amino-acids. Charged amino-acids are normally not present in this region. The membrane spanning region is followed by the recognition site for signal peptidase. The recognition site consists of amino-acids with the preference for small-X-small. Small amino-acids can be alanine, glycine, serine or cysteine. X can be any amino acids. Using such rules an algorithm has been written that is able to recognize such signal sequences from eukaryotes and prokaryotes (Bendtsen, Nielsen, von Heijne and Brunak. (2004) J. Mol. Biol., 340:783-795). The SignalP program to calculate and recognize signal sequences in proteins is generally available httpcolonforwardslashforwardslashwwwdotcbsdotdtudotdkforwardslashservicesforward slashSiQnalPforwardslash).

Relevant for the present invention is that signal sequences can be recognized from the deduced protein sequence of a sequenced gene. If a gene encodes a protein where a signal sequence is predicted using the SignalP program, the chance that this protein is secreted is high.

In a second embodiment, the present invention provides an isolated polypeptide which has sialidase activity, and is encoded by polynucleotides which hybridize or are capable of hybridizing under low stringency conditions, more preferably medium stringency conditions, and most preferably high stringency conditions, with (i) the nucleic acid sequence of SEQ ID NO:1 or (ii) a nucleic acid fragment comprising at least a portion of SEQ ID NO:1, or (iii) having bases differing from the bases of SEQ ID NO:1; or (iv) with a nucleic acid strand complementary to SEQ ID NO:1.

The term "capable of hybridizing" means that the target polynucleotide of the invention can hybridize to the nucleic acid used as a probe (for example, the nucleotide sequence set forth in SEQ ID NO: 1, or a fragment thereof, or the complement of SEQ ID NO: 1, or a fragment thereof) at a level significantly above background. The invention also includes the polynucleotides that encode the sialidase of the invention, as well as nucleotide sequences which are complementary thereto. The nucleotide sequence may be RNA or DNA, including genomic DNA, synthetic DNA or cDNA. Preferably, the nucleotide sequence is DNA and most preferably, a genomic DNA sequence. Typically, a polynucleotide of the invention comprises a contiguous sequence of nucleotides which is capable of hybridizing under selective conditions to the coding sequence or the complement of the coding sequence of SEQ ID NO: 1. Such nucleotides can be synthesized according to methods well known in the art.

A polynucleotide of the invention can hybridize to the coding sequence or the complement of the coding sequence of SEQ ID NO: 2 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 2 is typically at least 10 fold, preferably at least 20 fold, more preferably at least 50 fold, and even more preferably at least 100 fold, as intense as interactions between other polynucleotides and the coding sequence of SEQ ID NO: 2. The intensity of interaction may be measured, for example, by radiolabelling the probe, for example with $^{32}$P. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.).

A polynucleotide of the invention also includes synthetic genes that can encode for the polypeptide of SEQ ID NO: 3 or variants thereof. It is sometimes preferable to adapt the codon usage of a gene to the preferred bias in a production host. Techniques to design and construct synthetic genes are generally available (i.e. httpcolonforwardslashforwardslashwwwdotdnatwopointodotcomforwardslash).

Modifications

Polynucleotides of the invention may comprise DNA or RNA. They may be single or double stranded. They may also be polynucleotides which include within them synthetic or modified nucleotides including peptide nucleic acids. A number of different types of modifications to polynucleotides are known in the art. These include a methylphosphonate and phosphorothioate backbones, and addition of acridine or polylysine chains at the 3' and/or 5' ends of the molecule. For the purposes of the present invention, it is to be understood that the polynucleotides described herein may be modified by any method available in the art.

It is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The coding sequence of SEQ ID NO: 2 may be modified by nucleotide substitutions, for example from 1, 2 or 3 to 10, 25, 50, 100, or more substitutions. The polynucleotide of SEQ ID NO: 2 may alternatively or additionally be modified by one or more insertions and/or deletions and/or by an extension at either or both ends. The modified polynucleotide generally encodes a polypeptide which has sialidase activity. Degenerate substitutions may be made and/or substitutions may be made which would result in a conservative amino acid substitution when the modified sequence is translated, for example as discussed with reference to polypeptides later.

Homologues

A nucleotide sequence which is capable of selectively hybridizing to the complement of the DNA coding sequence of SEQ ID NO:2 is included in the invention and will generally have at least 50% or 60%, at least 70%, at least 80%, at least 90%, at least 95%, at least 98% or at least 99% sequence identity to the coding sequence of SEQ ID NO:2 over a region of at least 60, preferably at least 100, more preferably at least 200 contiguous nucleotides or most preferably over the full length of SEQ ID NO:2. Likewise, a nucleotide which encodes an active sialidase and which is capable of selectively hybridizing to a fragment of a complement of the DNA coding sequence of SEQ ID NO:2, is also embraced by the invention.

Any combination of the above mentioned degrees of identity and minimum sizes may be used to define polynucleotides of the invention, with the more stringent combinations (i.e. higher identity over longer lengths) being preferred. Thus, for example, a polynucleotide which is at least 80% or 90% identical over 60, preferably over 100 nucleotides, forms one aspect of the invention, as does a polynucleotide which is at least 90% identical over 200 nucleotides.

The BLAST N algorithm can be used to calculate sequence identity or to line up sequences (such as identifying equivalent or corresponding sequences, for example on their default settings).

Software for performing BLAST analyses is publicly available through the National Center for Biotechnology Information httpcolonforwardslashforwardslashwwwdotncbidotnlmdotnihdotpovforwardslash). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold. These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix alignments (B) of 50, expectation (E) of 10, M=5, N=4, and a comparison of both strands.

The BLAST algorithm performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Primers and Probes

Polynucleotides of the invention include and may be used as primers, for example as polymerase chain reaction (PCR) primers, as primers for alternative amplification reactions, or as probes for example labeled with a revealing label by conventional means using radioactive or non-radioactive labels, or the polynucleotides may be cloned into vectors. Such primers, probes and other fragments will be at least 15, for example at least 20, 25, 30 or 40 nucleotides in length. They will typically be up to 40, 50, 60, 70, 100, 150, 200 or 300 nucleotides in length, or even up to a few nucleotides (such as 5 or 10 nucleotides) short of the coding sequence of SEQ ID NO: 2.

In general, primers will be produced by synthetic means, involving a step-wise manufacture of the desired nucleic acid sequence one nucleotide at a time. Techniques for accomplishing this and protocols are readily available in the art. Longer polynucleotides will generally be produced using recombinant means, for example using PCR cloning techniques. This will involve making a pair of primers (typically of about 15-30 nucleotides) to amplify the desired region of the sialidase to be cloned, bringing the primers into contact with mRNA, cDNA or genomic DNA obtained from a yeast, bacterial, plant, prokaryotic or fungal cell, preferably of an *Penicillium* strain, performing a polymerase chain reaction under conditions suitable for the amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector, such as described in Example 1.

Alternatively, synthetic genes can be constructed that encompass the coding region of the secreted sialidase or variants thereof. Polynucleotides that are altered in many positions, but still encode the same protein can be conveniently be designed and constructed using these techniques. This has as advantage that the codon usage can be adapted to the preferred expression host, so productivity of the protein in this host can be improved. Also the polynucleotide sequence of a gene can be changed to improve mRNA stability or reduced turnover. This can lead to improved expression of the desired protein or variants thereof. Additionally, the polynucleotide sequence can be changed in a synthetic gene such that mutations are made in the protein sequence that have a positive effect on secretion efficiency, stability, proteolytic vulnerability, temperature optimum, specific activity or other relevant properties for industrial production or application of the protein. Companies that provide services to construct synthetic genes and optimize codon usage are generally available.

Such techniques may be used to obtain all or part of the polynucleotides encoding the sialidase sequences described herein. Introns, promoter and trailer regions are within the scope of the invention and may also be obtained in an analogous manner (e.g. by recombinant means, PCR or cloning techniques), starting with genomic DNA from a fungal, yeast, bacterial plant or prokaryotic cell.

The polynucleotides or primers may carry a revealing label. Suitable labels include radioisotopes such as $^{32}$P or $^{35}$S, fluorescent labels, enzyme labels, or other protein labels such as biotin. Such labels may be added to polynucleotides or primers of the invention and may be detected using techniques known to persons skilled in the art.

Polynucleotides or primers (or fragments thereof) labeled or unlabelled may be used in nucleic acid-based tests for detecting or sequencing a sialidase or a variant thereof in a fungal sample. Such detection tests will generally comprise bringing a fungal sample suspected of containing the DNA of interest into contact with a probe comprising a polynucleotide or primer of the invention under hybridizing conditions, and detecting any duplex formed between the probe and nucleic acid in the sample. Detection may be achieved using techniques such as PCR or by immobilizing the probe on a solid support, removing any nucleic acid in the sample which is not hybridized to the probe, and then detecting any nucleic acid which is hybridized to the probe. Alternatively, the sample nucleic acid may be immobilized on a solid support, the probe hybridized and the amount of probe bound to such a support after the removal of any unbound probe detected.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like. The probes and polynucleotides of the invention may also be used in microassay.

Preferably, the polynucleotide of the invention is obtainable from the same organism as the polypeptide, such as a fungus, in particular a fungus of the genus *Aspergillus*.

Production of Polynucleotides

Polynucleotides which do not have 100% identity with SEQ ID NO: 2 but fall within the scope of the invention can be obtained in a number of ways. Thus, variants of the sialidase sequence described herein may be obtained for example, by probing genomic DNA libraries made from a range of organisms, such as those discussed as sources of the polypeptides of the invention. In addition, other fungal, plant or prokaryotic homologues of sialidase may be obtained and such homologues and fragments thereof in general will be capable of hybridising to SEQ ID NO:1. Such sequences may be obtained by probing cDNA libraries or genomic DNA libraries from other species, and probing such libraries with probes comprising all or part of SEQ ID NO:1 under conditions of low, medium to high stringency (as described earlier). Nucleic acid probes comprising all or part of SEQ ID NO: 1 may be used to probe cDNA or genomic libraries from other species, such as those described as sources for the polypeptides of the invention.

Species homologues may also be obtained using degenerate PCR, which uses primers designed to target sequences within the variants and homologues which encode conserved amino acid sequences. The primers can contain one or more degenerate positions and will be used at stringency conditions lower than those used for cloning sequences with single sequence primers against known sequences.

Alternatively, such polynucleotides may be obtained by site directed mutagenesis of the sialidase sequences or variants thereof. This may be useful where, for example, silent codon changes to sequences are required to optimize codon preferences for a particular host cell in which the polynucleotide sequences are being expressed. Other sequence changes may be made in order to introduce restriction enzyme recognition sites, or to alter the property or function of the polypeptides encoded by the polynucleotides.

The invention includes double stranded polynucleotides comprising a polynucleotide of the invention and its complement.

The present invention also provides polynucleotides encoding the polypeptides of the invention described above. Since such polynucleotides will be useful as sequences for recombinant production of polypeptides of the invention, it is not necessary for them to be capable of hybridising to the sequence of SEQ ID NO: 1 or SEQ ID NO:2, although this will generally be desirable. Otherwise, such polynucleotides may be labeled, used, and made as described above if desired.

Recombinant Polynucleotides

The invention also provides vectors comprising a polynucleotide of the invention, including cloning and expression vectors, and in another aspect methods of growing, transforming or transfecting such vectors into a suitable host cell, for example under conditions in which expression of a polypeptide of, or encoded by a sequence of, the invention occurs. Provided are host cells comprising a polynucleotide or vector of the invention wherein the polynucleotide is heterologous to the genome of the host cell. The term "heterologous", usually with respect to the host cell, means that the polynucleotide does not naturally occur in the genome of the host cell or that the polypeptide is not naturally produced by that cell. Preferably, the host cell is a yeast cell, for example a yeast cell of the genus *Kluyveromyces, Pichia, Hansenula* or *Saccharomyces* or a filamentous fungal cell, for example of the genus *Aspergillus, Penicillium, Trichoderma* or *Fusarium*.

Vectors

The vector into which the expression cassette of the invention is inserted may be any vector that may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, such as a plasmid. Alternatively, the vector may be one which, when introduced into a host cell, is integrated into the host cell genome and replicates together with the chromosome(s) into which it has been integrated.

Preferably, when a polynucleotide of the invention is in a vector it is operably linked to a regulatory sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under production conditions.

The vectors may, for example in the case of plasmid, cosmid, virus or phage vectors, be provided with an origin of replication, optionally a promoter for the expression of the polynucleotide and optionally an enhancer and/or a regulator of the promoter. A terminator sequence may be present, as may be a polyadenylation sequence. The vectors may contain one or more selectable marker genes, for example an ampicillin resistance gene in the case of a bacterial plasmid or a neomycin resistance gene for a mammalian vector. Vectors may be used in vitro, for example for the production of RNA or can be used to transfect or transform a host cell.

The DNA sequence encoding the polypeptide is preferably introduced into a suitable host as part of an expression construct in which the DNA sequence is operably linked to expression signals which are capable of directing expression of the DNA sequence in the host cells. For transformation of the suitable host with the expression construct transformation procedures are available which are well known to the skilled person. The expression construct can be used for transformation of the host as part of a vector carrying a selectable marker, or the expression construct is co-transformed as a separate molecule together with the vector carrying a selectable marker. The vectors may contain one or more selectable marker genes.

Preferred selectable markers include but are not limited to those that complement a defect in the host cell or confer resistance to a drug. They include for example versatile marker genes that can be used for transformation of most filamentous fungi and yeasts such as acetamidase genes or cDNAs (the amdS, niaD, facA genes or cDNAs from *A. nidulans, A. oryzae,* or *A. niger*), or genes providing resistance to antibiotics like G418, hygromycin, bleomycin, kanamycin, phleomycin or benomyl resistance (benA). Alternatively, specific selection markers can be used such as auxotrophic markers which require corresponding mutant host strains: e.g. URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase subunit 9 (oliC), orotidine-5'-phosphate-decarboxylase (pvrA), the bacterial G418 resistance gene (useful in yeast, but not in filamentous fungi), the ampicillin resistance gene (*E. coli*), the neomycin resistance gene (*Bacillus*) and the *E. coli* uidA gene, coding for glucuronidase (GUS). Vectors may be used in vitro, for example for the production of RNA or to transfect or transform a host cell.

For most filamentous fungi and yeast, the expression construct is preferably integrated into the genome of the host cell in order to obtain stable transformants. However, for certain yeasts suitable episomal vector systems are also available into which the expression construct can be incorporated for stable and high level expression. Examples thereof include vectors derived from the 2 μm, CEN and pKD1 plasmids of *Saccharomyces* and *Kluyveromyces*, respectively, or vectors containing an AMA sequence (e.g. AMA1 from *Aspergillus*). When expression constructs are integrated into host cell genomes, the constructs are either integrated at random loci in the genome, or at predetermined target loci using homologous recombination, in which case the target loci preferably comprise a highly expressed gene. A highly expressed gene is a gene whose mRNA can make up at least 0.01% (w/w) of the total cellular mRNA, for example under induced conditions, or alternatively, a gene whose gene product can make up at least 0.2% (w/w) of the total cellular protein, or, in case of a secreted gene product, can be secreted to a level of at least 0.05 g/l.

An expression construct for a given host cell will usually contain the following elements operably linked to each other in consecutive order from the 5'-end to 3'-end relative to the coding strand of the sequence encoding the polypeptide of the first aspect: (1) a promoter sequence capable of directing transcription of the DNA sequence encoding the polypeptide in the given host cell, (2) preferably, a 5'-untranslated region (leader), (3) optionally, a signal sequence capable of directing secretion of the polypeptide from the given host cell into the culture medium, (4) the DNA sequence encoding a mature and preferably active form of the polypeptide, and preferably also (5) a transcription termination region (terminator) capable of terminating transcription downstream of the DNA sequence encoding the polypeptide.

Downstream of the DNA sequence encoding the polypeptide, the expression construct preferably contains a 3' untranslated region containing one or more transcription termination sites, also referred to as a terminator. The origin of the terminator is less critical. The terminator can for example be native to the DNA sequence encoding the polypeptide. However, preferably a bacterial terminator is used in bacterial host cells, a yeast terminator is used in yeast host cells and a filamentous fungal terminator is used in filamentous fungal host cells. More preferably, the terminator is endogenous to the host cell in which the DNA sequence encoding the polypeptide is expressed.

Enhanced expression of the polynucleotide encoding the polypeptide of the invention may also be achieved by the selection of heterologous regulatory regions, e.g. promoter, signal sequence and terminator regions, which serve to increase expression and, if desired, secretion levels of the protein of interest from the chosen expression host and/or to provide for the inducible control of the expression of the polypeptide of the invention.

Aside from the promoter native to the gene encoding the polypeptide of the invention, other promoters may be used to direct expression of the polypeptide of the invention. The promoter may be selected for its efficiency in directing the expression of the polypeptide of the invention in the desired expression host.

Promoters/enhancers and other expression regulation signals may be selected to be compatible with the host cell for which the expression vector is designed. For example prokaryotic promoters may be used, in particular those suitable for use in *E. coli* strains. When expression of the polypeptides of the invention is carried out in mammalian cells, mammalian promoters may be used. Tissues-specific promoters, for example hepatocyte cell-specific promoters, may also be used. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, herpes simplex virus promoters or adenovirus promoters.

Suitable yeast promoters include the *S. cerevisiae* GAL4 and ADH promoters and the *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as β-actin promoters, may be used. Tissue-specific promoters, in particular endothelial or neuronal cell specific promoters (for example the DDAHI and DDAHII promoters), are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

A variety of promoters can be used that are capable of directing transcription in the host cells of the invention. Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which are preferred for use in fungal expression hosts are those which are obtainable from the fungal genes for xylanase (xlnA), phytase, ATP-synthetase subunit 9 (oliC), triose phosphate isomerase (tpi), alcohol dehydrogenase (AdhA), amylase (amy), amyloglucosidase (AG—from the glaA gene), acetamidase (amdS) and glyceraldehyde-3-phosphate dehydrogenase (gpd) promoters.

Examples of strong yeast promoters which may be used include those obtainable from the genes for alcohol dehydrogenase, glyceraldehyde-3-phosphate dehydrogenase, lactase, 3-phosphoglycerate kinase, plasma membrane ATPase (PMA1) and triosephosphate isomerase.

Examples of strong bacterial promoters which may be used include the amylase and SPo2 promoters as well as promoters from extracellular protease genes.

Promoters suitable for plant cells which may be used include napaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters.

The vector may further include sequences flanking the polynucleotide giving rise to RNA which comprise sequences homologous to ones from eukaryotic genomic sequences, preferably fungal genomic sequences, or yeast genomic sequences. This will allow the introduction of the polynucleotides of the invention into the genome of fungi or yeasts by homologous recombination. In particular, a plasmid vector comprising the expression cassette flanked by fungal sequences can be used to prepare a vector suitable for delivering the polynucleotides of the invention to a fungal cell. Transformation techniques using these fungal vectors are known to those skilled in the art.

The vector may contain a polynucleotide of the invention oriented in an antisense direction to provide for the production of antisense RNA. This may be used to reduce, if desirable, the levels of expression of the polypeptide.

Host Cells and Expression

In a further aspect the invention provides a process for preparing a polypeptide of the invention which comprises cultivating a host cell transformed or transfected with an expression vector as described above under conditions suitable for expression by the vector of a coding sequence encoding the polypeptide, and recovering the expressed polypeptide. Polynucleotides of the invention can be incorporated into a recombinant replicable vector, such as an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. Suitable host cells include bacteria such as *E. coli*, yeast, mammalian cell lines and other eukaryotic cell lines, for example insect cells such as Sf9 cells and (e.g. filamentous) fungal cells.

Preferably the polypeptide is produced as a secreted protein in which case the DNA sequence encoding a mature form of the polypeptide in the expression construct may be operably linked to a DNA sequence encoding a signal sequence. In the case where the gene encoding the secreted protein has in the wild type strain a signal sequence preferably the signal sequence used will be native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast MFalpha genes. Similarly, a suitable signal sequence for filamentous fungal host cells is e.g. a signal sequence derived from a filamentous fungal amyloglucosidase (AG) gene, e.g. the *A. niger* glaA gene. This signal sequence may be used in combination with the amyloglucosidase (also called (gluco) amylase) promoter itself, as well as in combination with other promoters. Hybrid signal sequences may also be used within the context of the present invention.

Preferred heterologous secretion leader sequences are those originating from the fungal amyloglucosidase (AG) gene (glaA—both 18 and 24 amino acid versions e.g. from *Aspergillus*), the MFalpha gene (yeasts e.g. *Saccharomyces, Pichia* and *Kluyveromyces*) or the alpha-amylase gene (*Bacillus*).

The vectors may be transformed or transfected into a suitable host cell as described above to provide for expression of a polypeptide of the invention. This process may comprise culturing a host cell transformed with an expression vector as described above under conditions suitable for expression of the polypeptide, and optionally recovering the expressed polypeptide.

A further aspect of the invention thus provides host cells transformed or transfected with or comprising a polynucleotide or vector of the invention. Preferably the polynucleotide is carried in a vector which allows the replication and expression of the polynucleotide. The cells will be chosen to be compatible with the said vector and may for example be prokaryotic (for example bacterial), or eukaryotic fungal, yeast or plant cells.

The invention encompasses processes for the production of a polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is herein defined as a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over filamentous fungal cells because they are easier to manipulate. However, some proteins are either poorly secreted from yeasts, or in some cases are not processed properly (e.g. hyperglycosylation in yeast). In these instances, a filamentous fungal host organism should be selected.

Bacteria from the genus *Bacillus* are very suitable as heterologous hosts because of their capability to secrete proteins into the culture medium. Other bacteria suitable as hosts are those from the genera *Streptomyces* and *Pseudomonas*. A preferred yeast host cell for the expression of the DNA sequence encoding the polypeptide is one of the genus *Saccharomyces, Kluyveromyces, Hansenula, Pichia, Yarrowia*, or *Schizosaccharomyces*. More preferably, a yeast host cell is selected from the group consisting of the species *Saccharomyces cerevisiae, Kluyveromyces lactis* (also known as *Kluyveromyces marxianus* var. *lactis*), *Hansenula polymorpha, Pichia pastoris, Yarrowia lipolytica*, and *Schizosaccharomyces pombe*.

Most preferred for the expression of the DNA sequence encoding the polypeptide are, however, filamentous fungal host cells. Preferred filamentous fungal host cells are selected from the group consisting of the genera *Aspergillus, Trichoderma, Fusarium, Disporotrichum, Penicillium, Acremonium, Neurospora, Thermoascus, Myceliophtora, Sporotrichum, Thielavia,* and *Talaromyces*. More preferably a filamentous fungal host cell is of the species *Aspergillus oryzae, Aspergillus sojae* or *Aspergillus nidulans* or is of a species from the *Aspergillus niger* Group (as defined by Raper and Fennell, The Genus *Aspergillus*, The Williams & Wilkins Company, Baltimore, pp 293-344, 1965). These include but are not limited to *Aspergillus niger, Aspergillus awamori, Aspergillus tubigensis, Aspergillus aculeatus, Aspergillus foetidus, Aspergillus nidulans, Aspergillus japonicus, Aspergillus otyzae* and *Aspergillus ficuum*, and also those of the species *Trichoderma reesei, Fusarium graminearum, Penicillium chrysogenum, Acremonium alabamense, Neurospora crassa, Myceliophtora thermophilum, Sporotrichum cellulophilum, Disporotrichum dimorphosphorum* and *Thielavia terrestris*.

Examples of preferred expression hosts within the scope of the present invention are fungi such as *Aspergillus* species (in particular those described in EP-A-184,438 and EP-A-284,603) and *Trichoderma* species; bacteria such as *Bacillus* species (in particular those described in EP-A-134,048 and EP-A-253,455), especially *Bacillus subtilis, Bacillus licheniformis, Bacillus amyloliquefaciens, Pseudomonas* species; and yeasts such as *Kluyveromyces* species (in particular those described in EP-A-096,430 such as *Kluyveromyces lactis* and in EP-A-301,670) and *Saccharomyces* species, such as *Saccharomyces cerevisiae*.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (typically stably) into its genome a sequence encoding the polypeptides of the invention. The transformation of plant cells can be performed using known techniques, for example using a Ti or a Ri plasmid from *Agrobacterium tumefaciens*. The plasmid (or vector) may thus contain sequences necessary to infect a plant, and derivatives of the Ti and/or Ri plasmids may be employed.

The host cell may overexpress the polypeptide, and techniques for engineering over-expression are well known and can be used in the present invention. The host may thus have two or more copies of the polynucleotide.

Alternatively, direct infection of a part of a plant, such as a leaf, root or stem can be effected. In this technique the plant to be infected can be wounded, for example by cutting the plant with a razor, puncturing the plant with a needle or rubbing the plant with an abrasive. The wound is then innoculated with the *Agrobacterium*. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.

Culture of Host Cells and Recombinant Production

The invention also includes cells that have been modified to express the sialidase or a variant thereof. Such cells include transient, or preferably stably modified higher eukaryotic cell lines, such as mammalian cells or insect cells, lower eukaryotic cells, such as yeast and filamentous fungal cells or prokaryotic cells such as bacterial cells.

It is also possible for the polypeptides of the invention to be transiently expressed in a cell line or on a membrane, such as for example in a baculovirus expression system. Such systems, which are adapted to express the proteins according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culturing is ceased and the polypeptide is recovered using known procedures.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (dependent on the expression construct used) may be included or subsequently be added.

The selection of the appropriate medium may be based on the choice of expression host and/or based on the regulatory requirements of the expression construct. Suitable media are well-known to those skilled in the art. The medium may, if desired, contain additional components favoring the transformed expression hosts over other potentially contaminating microorganisms.

The fermentation may be performed over a period of from 0.5-30 days. Fermentation may be a batch, continuous or fed-batch process, at a suitable temperature in the range of between 0° C. and 45° C. and, for example, at a pH from 2 to 10. Preferred fermentation conditions include a temperature in the range of between 20° C. and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means. The sialidase of the invention can be purified from fungal mycelium or from the culture broth into which the sialidase is released by the cultured fungal cells.

In a preferred embodiment the polypeptide produced from a fungus, more preferably from an *Aspergillus*, most preferably from *Aspergillus niger*.

Modifications

Polypeptides of the invention may be chemically modified, e.g. post-translationally modified. For example, they may be glycosylated (one or more times) or comprise modified amino acid residues. They may also be modified by the addition of histidine residues to assist their purification or by the addition of a signal sequence to promote secretion from the cell. The polypeptide may have amino- or carboxyl-terminal extensions, such as an amino-terminal methionine residue, a small linker peptide of up to about 20-25 residues, or a small extension that facilitates purification, such as a poly-histidine tract, an antigenic epitope or a binding domain.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

The polypeptides may be modified to include non-naturally occurring amino acids or to increase the stability of the polypeptide. When the proteins or peptides are produced by synthetic means, such amino acids may be introduced during production. The proteins or peptides may also be modified following either synthetic or recombinant production.

The polypeptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with $NaBH_4$, amidination with methylacetimidate or acylation with acetic anhydride.

The sequences provided by the present invention may also be used as starting materials for the construction of "second generation" enzymes. "Second generation" sialidases are sialidases, altered by mutagenesis techniques (e.g. site-directed mutagenesis or gene shuffling techniques), which have properties that differ from those of wild-type sialidase or recombinant sialidase such as those produced by the present invention. For example, their temperature or pH optimum, specific activity, substrate affinity or thermostability may be altered so as to be better suited for use in a particular process.

Amino acids essential to the activity of the sialidase of the invention, and therefore preferably subject to substitution, may be identified according to procedures known in the art, such as site-directed mutagenesis or alanine-scanning mutagenesis. In the latter technique mutations are introduced at every residue in the molecule, and the resultant mutant molecules are tested for biological activity (e.g. sialidase activity) to identify amino acid residues that are critical to the activity of the molecule. Sites of enzyme-substrate interaction can also be determined by analysis of crystal structure as determined by such techniques as nuclear magnetic resonance, crystallography or photo-affinity labeling.

Gene shuffling techniques provide a random way to introduce mutations in a polynucleotide sequence. After expression the isolates with the best properties are re-isolated, combined and shuffled again to increase the genetic diversity. By repeating this procedure a number of times, genes that code for fastly improved proteins can be isolated. Preferably the gene shuffling procedure is started with a family of genes that code for proteins with a similar function. The family of polynucleotide sequences provided with this invention would be well suited for gene shuffling to improve the properties of secreted sialidases.

Alternatively classical random mutagenesis techniques and selection, such as mutagenesis with NTG treatment or UV mutagenesis, can be used to improve the properties of a protein. Mutagenesis can be performed directly on isolated DNA, or on cells transformed with the DNA of interest. Alternatively, mutations can be introduced in isolated DNA by a number of techniques that are known to the person skilled in the art. Examples of these methods are error-prone PCR, amplification of plasmid DNA in a repear-deficient host cell, etc.

The use of yeast and filamentous fungal host cells is expected to provide for post-translational modifications (e.g. proteolytic processing, myristilation, glycosylation, truncation, and tyrosine, serine or threonine phosphorylation) as may be needed to confer optimal biological activity on recombinant expression products of the invention.

Preparations

Polypeptides of the invention may be in an isolated form. It will be understood that the polypeptide may be mixed with carriers or diluents which will not interfere with the intended purpose of the polypeptide and still be regarded as isolated. A polypeptide of the invention may also be in a substantially purified form, in which case it will generally comprise the polypeptide in a preparation in which more than 70%, e.g. more than 80%, 90%, 95%, 98% or 99% of the proteins in the preparation is a polypeptide of the invention.

Polypeptides of the invention may be provided in a form such that they are outside their natural cellular environment. Thus, they may be substantially isolated or purified, as discussed above, or in a cell in which they do not occur in nature, for example a cell of other fungal species, animals, plants or bacteria.

Removal or Reduction of Sialidase Activity

The present invention also relates to methods for producing a mutant cell of a parent cell, which comprises disrupting or deleting the endogenous nucleic acid sequence encoding the polypeptide or a control sequence thereof, which results in the mutant cell producing less of the polypeptide than the parent cell.

The construction of strains which have reduced sialidase activity may be conveniently accomplished by modification or inactivation of a nucleic acid sequence necessary for expression of the sialidase in the cell. The nucleic acid sequence to be modified or inactivated may be, for example, a nucleic acid sequence encoding the polypeptide or a part thereof essential for exhibiting sialidase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification include, but are not limited to, a leader sequence, a polyadenylation sequence, a propeptide sequence, a signal sequence, and a termination sequence.

Modification or inactivation of the nucleic acid sequence may be performed by subjecting the cell to mutagenesis and selecting cells in which the sialidase producing capability has been reduced or eliminated. The mutagenesis, which may be specific or random, may be performed, for example, by use of a suitable physical or chemical mutagenizing agent, by use of a suitable oligonucleotide, or by subjecting the DNA sequence to PCR mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (NTG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced or no expression of sialidase activity.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR mutagenesis in accordance with methods known in the art.

Although, in principle, the modification may be performed in vivo, i.e., directly on the cell expressing the nucleic acid sequence to be modified, it is preferred that the modification be performed in vitro as exemplified below.

An example of a convenient way to inactivate or reduce production of the sialidase by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. Preferably the defective gene or gene fragment also encodes a marker which may be used to select for transformants in which the gene encoding the polypeptide has been modified or destroyed.

Alternatively, modification or inactivation of the nucleic acid sequence encoding a polypeptide of the present invention may be achieved by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide. The antisense polynucleotide will then typically be transcribed in the cell and will be capable of hybridizing to the mRNA encoding the sialidase. Under conditions allowing the complementary antisense nucleotide sequence to hybridize to the mRNA, the amount of the sialidase produced in the cell will be reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of the endogenous nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) culturing the mutant cell under conditions conducive for production of the polypeptide; and (b) recovering the polypeptide. In the present context, the term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a still further aspect, the present invention provides a method for producing a protein product essentially free of sialidase activity by fermentation of a cell which produces both an sialidase polypeptide of the present invention as well as the protein product of interest. The method comprises adding an effective amount of an agent capable of inhibiting sialidase activity to the fermentation broth either during or after the fermentation has been completed, recovering the product of interest from the fermentation broth, and optionally subjecting the recovered product to further purification. Alternatively, after cultivation the resultant culture broth can be subjected to a pH or temperature treatment so as to reduce the sialidase activity substantially, and allow recovery of the product from the culture broth. The combined pH or temperature treatment may be performed on an protein preparation recovered from the culture broth.

The methods of the present invention for producing an essentially sialidase-free product is of particular interest in the production of eukaryotic polypeptides, in particular in the production of fungal proteins such as enzymes. The sialidase-deficient cells may also be used to express heterologous proteins of interest for the food industry, or of pharmaceutical interest.

Cheese Making and Milk Coagulation

Coagulation is an essential step in the traditional production of cheese from a dairy composition such as bovine milk. The coagulation may be started by acidification and/or the addition of an enzyme (coagulant) such as chymosine. After coagulation, the milk is separated into curd and whey. The curd is processed further into cheese.

Cheese manufacturing processes from various milk sources have long been known and have been described in detail for many different types of cheese variants. (see e.g. Cheese: Chemistry, Physics and Microbiology, Vol 1&2, 1999, Ed. Fox, Aspen Publications, Gaithersburg, Md.; Encyclopedia of Dairy Sciences Vol 1-4, 2003, Academic Press, London). A crucial point in cheese manufacture is the process of coagulation, in which the solubility of the casein micelles and submicelles is decreased. Enzyme induced coagulation is very commonly used. Enzymes like calf chymosine, microbial equivalents of chymosine and other enzymes from other sources have been described and several are available under various trade names. All of them can be used to initiate the coagulation process. The primary step in coagulation is the cleavage of the $Phe_{105}$-$Met_{106}$ bond in κ-casein. This leads to removal of the C-terminal part of κ-casein: the glycomacropeptide (GMP). Removal of the GMP leads to association of the casein micelles, i.e. casein coagulation. Casein coagulation leads to gel formation, and the time required to obtain gelling in a particular dairy composition is directly related to the activity of the coagulant.

The time that passes between addition of the coagulant and appearance of initial casein flocculation is defined as the coagulation time. The speed at which the gel is formed in cheese milk and the compactness of the gel depend closely on the quantity of enzyme added, the concentration of calcium ions, phosphorous, temperature and the pH. After the initial coagulation, a gel is formed and the consistency of the gel increases following an increase in the inter-micellar bonds. The micelles move together and the coagulum contracts, hereby expelling the whey. This phenomenon is known as syneresis and is accelerated by cutting the curd, increasing the temperature and increasing the acidity produced by the developing lactic acid bacteria.

The time between addition of coagulant and the start of the cutting of the gel to initiate syneresis will in the remainder of this text be referred to as curdling time. The curdling time is constant for a particular cheese variety in a specific cheese making factory, although small variations (up to 5-10%) may occur as a result of changes in quality of e.g. the milk or the coagulant. In many cheese making factories, the curdling time is the time limiting step in the process. When the curdling time is reduced, the factory can process more milk into curd, which is than further processed into cheese. A reduction in curdling time is therefore of economic interest, and there is a need for such reduced curdling time.

The curdling time can be reduced in several ways, such as an increase in added coagulant, lowering the pH of the milk or increased levels of added calcium chloride. These solutions are, however, not broadly used in the cheese making industry because they negatively affect the quality of the cheese. Increased levels of coagulant often lead to the formation of bitter taste as a result of unbalanced protease activities. A reduction in milk pH leads to a curd that is of inferior quality and often leads to yield losses. Increase of calcium chloride concentrations negatively affects taste and is often limited by legislation. There is no method currently available to reduce the curdling time without negative side effects.

The stability of the casein micelles against aggregation is of crucial importance in the aggregation process. The κ-casein plays a crucial role in casein micelle stabilization. Hydrophilic and negatively charged C-terminal parts of κ-casein chains located on the micelle surface are responsible for steric hindrance and electrostatic repulsion preventing coagulation of micellar casein (Minkiewicz et al, Pol J Food Nutr Sci (1993) 243, 39-48). κ-casein is a glycoprotein that contains sialic acid residues at known positions (Cases et al, J Food Sci (2003) 68, 2406-2410; Fournet et al, Biochim Biophys Acta (1979) 576, 339-346). It is known that there is a micro-heterogeneity in the population of κ-casein based due to differences in glycosylation and sialic acid content (Robitaille et al, Food Res Int (1995) 28, 17-21; Robitaille et al, J Dairy Res (1991) 58, 107-114). Several studies describe the effect removal of sialic acid residues using the sailidase derived from *Clostridium perfringens*. Parameters that were examined are the stability of the casein micelle against heat and chymosin degradation. Gibbons et al (Biochim Biophys Acta (1962) 56, 354-356) used solutions of purified κ-casein and showed that removal of sialic acid residues does not affect the action of chymosin on κ-casein. Vreeman et al (Biochem J (1986) 240, 87-97) compared the kinetic behaviour of chymosin towards purified κ-casein fractions with or without glycosylation and found that the deglycosylated κ-casein is a better substrate for chymosin. Also, Minkiewicz et al (Pol J Food Nutr Sci (1993), 243, 39-48) using an artificial reconstituted casein micelle system, showed that sialic acid residues are contributing the heat stability of casein micelles, which was later confirmed by Robitaille et al (Food Res Int (1995) 28, 17-21). In a separate study, Robitaille et al (Food Res Int (1993) 26, 365-369) showed that removal of sialic acid residues from κ-casein has no significant effect on the coagulation time but that the curd firmness decreased. No cheese making process has been described with a reduced curdling time but with unaffected cheese properties, and this remains an industrial need.

A recent patent application (EP1370146) describes a process in which a single glycosidases, including N-acetyl-neuraminidase is used to clot milk. In the described configuration, no enzyme coagulant is used. The omission of the coagulant opens the way for alternative cheese making processes but it is an unattractive process for traditional cheese making processes because the (proteolytic) coagulant is an important part of the proteolytic system in cheese that leads to the formation of characteristic flavour compounds (see e.g. Cheese: Chemistry, Physics and Microbiology, Vol 1&2, 1999, Ed. Fox, Aspen Publications, Gaithersburg, Md.; Encyclopedia of Dairy Sciences Vol 1-4, 2003, Academic Press, London for references on the role of chymosin in cheese flavour formation).

In the present context, the term 'cheese' refers to any kind of cheese such as e.g. natural cheese, cheese analogues and processed cheese. The cheese may be obtained by any suitable process known in the art such as e.g. by enzymatic coagulation of a dairy composition with rennet, or by acidic coagulation of a dairy composition with a food grade acid or acid produced by lactic acid bacteria growth. In one embodiment, the cheese is rennet-curd cheese. The dairy composition may be subjected to a conventional cheese-making process. Processed cheese is preferably manufactured from natural cheese or cheese analogues by cooking and emulsifying the cheese, such as with emulsifying salts (e.g. phosphates and citrate). The process may further include the addition of spices/condiments.

The term 'cheese analogues' refers to cheese-like products which contain fat (such as e.g. milk fat (e.g. cream) as part of the composition, and which further contain, as part of the composition, a non-milk constituent, such as e.g. vegetable oil. Cheese comprises all varieties of cheese, such as soft cheese, semi-hard cheese and hard cheese. In cheese manufacture, the coagulation of a dairy composition is preferably performed either by rennet or by acidification alone resulting in rennet-curd and acid-curd cheese, respectively. Fresh acid-curd cheeses refer to those varieties of cheese produced by the coagulation of milk, cream or whey via acidification or a combination of acid and heat, and which are ready for consumption once the manufacturing without ripening is completed. Fresh acid-curd cheeses generally differ from rennet-curd cheese varieties (e.g. Camembert, Cheddar, Emmenthal) where coagulation normally is induced by the action of rennet at pH values 6.4-6.6, in that coagulation normally occurs close to the iso-electric point of casein, i.e. e.g. at pH4.6 or at higher values when elevated temperatures are used, e.g. in Ricotta at pH typically about 6.0 and temperature typically about 80° C. In a preferred embodiment, the cheese belongs to the class of rennet curd cheeses.

A dairy composition may be any composition comprising cows milk constituents. Milk constituents may be any constituent of milk such as milk fat, milk protein, casein, whey protein and lactose. A milk fraction may be any fraction of milk such as e.g. skim milk, butter milk, whey, cream, milk powder, whole milk powder, skim milk powder. In a preferred embodiment the dairy composition comprises milk, skim milk, butter milk, whole milk, whey, cream, or any combination thereof. In a more preferred embodiment the dairy composition consists of milk, such as skim milk, whole milk, cream or any combination thereof. In further embodiments, the dairy composition is prepared, totally or in part, from dried milk fractions, such as e.g. whole milk powder, skim milk powder, casein, caseinate, total milk protein or buttermilk powder, or any combination thereof. A dairy composition comprises cow's milk and or one or more cow's milk fractions. The cow's milk fractions may be from any breed of cow (*Bos Taurus* (*Bos taurus taurus*), *Bos indicus* (*Bos indicus taurus*) and crossbreeds of these. In one embodiment the dairy composition comprises cow's milk and/or cow's milk fractions originating from two or more breeds of cows. The dairy composition also comprises milk from other mammals that are used for cheese preparation, such as milk derived from goat, buffalo or camel. The dairy composition for production of cheese may be standardized to the desired composition by removal of all or a portion of any of the raw milk components and/or by adding thereto additional amounts of such components. This may be done e.g. by separation of milk into cream and milk upon arrival to the dairy. Thus, the dairy composition may be prepared as done conventionally by fractionating milk and recombining the fractions so as to obtain the desired final composition of the dairy composition. The separation may be made in continuous centrifuges leading to a skim milk fraction with very low fat content (i.e. <0.5%) and cream with e.g. >35% fat. The dairy composition may be prepared by mixing cream and skim milk. In another embodiment the protein and/or casein content may be standardized by the use of ultra filtration. The dairy composition may have any total fat content that is found suitable for the cheese to be produced by the process of the invention.

Calcium may be added to the dairy composition at any appropriate step before and/or during cheese making, such as before, simultaneously with, or after addition of starter culture. In a preferred embodiment calcium is added both before and after the heat treatment. Calcium may be added in any suitable form. In a preferred embodiment calcium is added as calcium salt, e.g. as $CaCl_2$. Any suitable amount of calcium may be added to the dairy composition. The concentration of the added calcium will usually be in the range 0.1-5.0 mM, such as between 1 and 3 mM. If $CaCl_2$ is added to the dairy composition the amount will usually be in the range 1-50 g per 100 liter of dairy composition, such as in the range 5-30 g per 1000 liter dairy composition, preferably in the range 10-20 g per 100 liter dairy composition.

The bacterial count of skim milk may be lowered by conventional steps. The dairy composition may be subjected to a homogenization process before production of cheese, such as in the production of Danish Blue Cheese.

The invention is illustrated by the examples below.

EXAMPLES

Example 1

Cloning and Expression of the Sialidase Gene ZJW

*Penicillium chrysogenum* strain Wisconsin 54-1255 (ATCC28089) was grown for 3 days at 30 degrees Celsius in PDB (Potato dextrose broth, Difco) and chromosomal DNA was isolated from the mycelium using the Q-Biogene kit (catalog nr. 6540-600; Omnilabo International BV, Breda, the Netherlands), using the instructions of the supplier. This chromosomal DNA was used for the amplification of the coding sequence of the sialidase gene using PCR.

To specifically amplify the sialidase gene ZJW from the chromosomal DNA of *Penicillium chrysogenum* strain Wisconsin 54-1255 (ATCC28089), two PCR primers were designed. Primer sequences were partly obtained from a sequence that was found in the genomic DNA of *Penicillium chrysogenum* Wisconsin 54-1255 (ATCC28089) and is depicted in SEQ ID NO: 1. We found that this sequence has homology with sialidase sequences of *Actinomyces* and *Arthrobacter*. However, no homologous fungal sialidases have been described yet. It is therefore surprising that we were able to find a gene encoding a secreted sialidase from a fungus. We describe here for the first time the efficient expression and characterization of a secreted fungal sialidase. The protein sequence of the complete sialidase protein, including potential pre- and pro-sequences is depicted in SEQ ID NO: 3. The advantage of the fungal enzyme compared to the bacterial homologues is that the fungal enzyme can be easily overexpressed and secreted in amounts that are relevant for applications in the food industry.

```
Zjw-dir
5'-CCCTTAATTAACTCATAGGCATCATGCTATCTTCATTGATGTATTT

Zjw-rev
5'-TTAGGCGCGCCGTACATACATGTACACATAGACC
```

The first, direct PCR primer (ZJW-dir) contains 23 nucleotides ZJW coding sequence starting at the ATG start codon, preceeded by a 23 nucleotides sequence including a PacI restriction site (SEQ ID NO:4). The second, reverse primer (ZJW-rev) contains nucleotides complementary to the reverse strand of the region downstream of the ZJW coding sequence preceeded by an AscI restriction site (SEQ ID NO:5). Using these primers we were able to amplify a 1.4 kb sized fragment with chromosomal DNA from *Penicillium chrysogenum* strain Wisconsin 54-1255 (ATCC28089) as template. The thus obtained 1.4 kb sized fragment was isolated, digested with PacI and AscI and purified. The PacI/AscI fragment comprising the ZJW coding sequences was exchanged with the PacI/AscI phyA fragment from pGBFIN-5 (WO 99/32617). Resulting plasmid is the ZJW expression vector named pGBFINZJW (see FIG. 1). The expression vector pGBFINZJW was linearized by digestion with NotI, which removes all *E. coli* derived sequences from the expression vector. The digested DNA was purified using phenol:chloroform:isoamylalcohol (24:23:1) extraction and precipitation with ethanol. These vectors were used to transform *Aspergillus niger* CBS513.88. An *Aspergillus niger* transformation procedure is extensively described in WO 98/46772. It is also described how to select for transformants on agar plates containing acetamide, and to select targeted multicopy integrants. Preferably, *A. niger* transformants containing multiple copies of the expression cassette are selected for further generation of sample material. For the pGBFINZJW expression vector 30 *A. niger* transformants were purified; first by plating individual transformants on selective medium plates followed by plating a single colony on PDA (potato dextrose agar: PDB+1.5% agar) plates. Spores of individual transformants were collected after growth for 1 week at 30 degrees Celsius. Spores were stored refrigerated and were used for the inoculation of liquid media.

An *A. niger* strain containing multiple copies of the expression cassette was used for generation of sample material by cultivation of the strain in shake flask cultures. A useful method for cultivation of *A. niger* strains and separation of the mycelium from the culture broth is described in WO 98/46772. Cultivation medium was in CSM-MES (150 g maltose, 60 g Soytone (Difco), 15 g $(NH_4)_2SO_4$, 1 g $NaH_2PO_4.H_2O$, 1 g $MgSO_4.7H_2O$, 1 g L-arginine, 80 mg Tween-80, 20 g MES pH6.2 per liter medium). 5 ml samples were taken on day 4-8 of the fermentation, centrifuged for 10 min at 5000 rpm in a Hereaus labofuge RF and supernatants were stored at –20° C. until further analyses.

SDS-Page molecular weight (MW) determination: a sample is analysed by SDS-PAGE on the NuPAGE Novex Bis-Tris 4-12% gradient system using NuPAGE MES-SDS running buffer (Invitrogen (Breda—the Netherlands)). Samples are reduced before loading, using NuPAGE reducing agent according to the supplier's protocol. To estimate the molecular weight of the produced protein, marker proteins (SeeBlue Plus2 Pre-Stained Standard (Invitrogen)) are used. Gels are run and stained using Simply Blue Protein Strain (Invitrogen) according to the supplier's instructions and the molecular weight of the produced protein was estimated by comparison with the standard proteins. In the present example 13 microliter of the supernatant of the fermentation broth of the transformant was analyzed.

It became clear that transformants containing the pGBFIN-ZJW vector secreted a protein of apparent molecular weight of approximately 50 kDa when analyzed with SDS-PAGE. Since this is slightly larger than the molecular weight that is predicted from the protein sequence, we presume that after removal of the signal sequence some glycosylation takes place when *Penicillium chrysogenum* sialidase ZJW is secreted from *Aspergillus niger*.

Selected strains can be used for isolation and purification of a larger amount of fungal sialidase, when fermentation and down-stream processing is scaled up. This enzyme can than be used for further analysis, and for the use in diverse industrial applications.

Example 2

Purification and Characterization of the Sialidase

Sialidase was produced via fermentation as described in Example 1. Enzyme activity was measured using the Amplex Red neuraminidase assay kit (obtained from Invitrogen). Culture filtrate (100 ml) was diluted with milliQ-water to a conductivity of 4.8 mS/cm and concentrated to 70 ml by ultrafiltration using a Biomax-10 membrane (obtained from Millipore). The pH was adjusted to 6.0 using NaOH and the sample was loaded on a 5 ml HiTrapQ ion exchange column (obtained from Amersham, 5 ml/min), equilibrated in 20 mM sodium citrate (pH6.0). The flow through of the column, containing the sialidase, was collected and dialyzed against 25 mM Tris, HCl (pH7.0) and loaded on a 5 ml HiTrap Q FF (5 ml/min), equilibrated in the same buffer. The sialidase was present in the flow-through fraction and was collected. The enzyme solution was then dialyzed against 30 mM sodium citrate (pH4.0, buffer A) and applied on a 5 ml HiTrap SP column (obtained from Amersham, 5 ml/min), equilibrated in buffer A. After loading the enzyme, the column was washed with 3 column volumes of buffer A and the enzyme was eluted with a linear gradient of 20 column volumes from buffer A to buffer B (buffer B: 30 mM sodium-citrate, pH4.0 containing 1 M NaCl). Sialidase-containing fractions were identified and pooled. Protein concentration was determined with the Bradford reagent (obtained from Sigma), using bovine serum albumin as reference protein. The protein was >95% pure as judged by the absence of contaminating bands on sodium-dodecyl polyacrylamide gel electrophoresis. The sialidase migrates at an apparent molecular weight of 47 kD, which is slightly higher than the molecular weight of 42.7 kD, calculated on basis of the predicted amino acid sequence. The enzyme preparation is does not show proteolytic activity on a series of substrates ZAAXpNA (Z=benzoyl group, A=alanine, X=any amino acid residue, pNA=para-nitroanilide), indicating absence of endo-protease activity.

Example 3

Method of Preparation of Miniature Cheeses

Miniature cheeses were produced as described by Shakeel-Ur-Rehman et al. (Protocol for the manufacture of miniature cheeses in Lait, 78 (1998), 607-620). Pasteurized full fat homogenized cows milk was used, but raw cows milk or reconstituted cows milk can also be used. The milk was transferred to wide mouth plastic centrifuge bottles (200 mL per bottle) and cooled to 31° C. Subsequently, 1.8 Units of starter culture DS 5LT1 (DSM Gist B. V., Delft, The Netherlands) were added to each of the 200 ml of pasteurized milk in the centrifuge bottles and the milk was ripened for 20 minutes. Then, $CaCl_2$ (132 µL of a 1 mol·L$^{-1}$ solution per 200 mL ripened milk) was added. Finally the coagulant was added (0.04 IMCU per ml); when sialidase was used, this was added together with the coagulant. The milk solutions were held for 40-50 minutes at 31° C. until a coagulum was formed. The coagulum was cut manually by cutters of stretched wire, spaced 1 cm apart on a frame. Healing was allowed for 2 minutes followed by gently stirring for 10 minutes. After that, the temperature was increased gradually to 39° C. over 30 minutes under continuous stirring of the curd/whey mixture. Upon reaching a pH of 6.2 the curd/whey mixtures were centrifuged at room temperature for 60 minutes at 1,700 g. The whey was drained and the curds were held in a water bath at 36° C. The cheeses were inverted every 15 minutes until the pH had decreased to 5.2-5.3 and were then centrifuged at room temperature at 1,700 g for 20 minutes. After manufacture the cheeses were weighed.

Example 4

Method to Determine Cheese Curdling

Cheese curdling was followed using the Optigraph (Alliance Instruments, France), as described by Kubarsep et al (Acta Agric Scand Section A (2005) 55, 145-148). The clotting time of a standard milk substrate solution, after addition of a milk-clotting enzyme solution, was determined according to a standard procedure (IDF157 A [2]). Milk substrate solutions were prepared by adding 11 gram of low heat nonfat milk powder (Nilac, obtained from NIZO, The Netherlands) to 100 ml milliQ-water containing 4.5 mM $CaCl_2$. The milk solution was stirred with a magnetic stirrer for 30 minutes. To settle the milk, the solution was put away for 30 minutes at room temperature in the dark. The pH of the milk is about 6.5. The milk-clotting enzyme was diluted with milli-Q water in order to achieve a rennet coagulation time (r) between 8 and 15 minutes. 10 ml milk solution was transferred to the sample cuvettes of the Optigraph. The milk was adjusted to the reaction temperature of 32° C. 200 µl of the diluted enzyme sample was pipetted into a multiple spoon apparatus and added in one time to the milk. This handling is the starting point of the coagulation test. The enzymes and milk were mixed with the spoons, supplied with the Optigraph for this purpose. Coagulation was monitored for 45 minutes.

The invention claimed is:

1. An isolated polypeptide which has sialidase activity and comprises an amino acid sequence which has at least 90% amino acid sequence identity with the sequence of amino acids from position 34 to position 407 of SEQ ID NO:3.

2. The polypeptide of claim 1 which has a molecular weight of less than 55 kDa as determined by sodium dodecyl sulfate-polyacrylamide gel electrophoresis [SDS-PAGE].

3. The polypeptide of claim 1 which has a molecular weight of less than 52 kDa as determined by SDS-PAGE.

4. The polypeptide of claim 1 which is an extracellular sialidase.

5. The polypeptide of claim 1 the amino acid sequence of which has at least 95% identity with the sequence of amino acids from position 34 to position 407 of SEQ ID NO:3.

6. The polypeptide of claim 1 the amino acid sequence of which has at least 97% identity with the sequence of amino acids from position 34 to position 407 of SEQ ID NO:3.

7. The polypeptide of claim 1, comprising the amino acid sequence of SEQ ID NO:3.

8. The polypeptide of claim 1, which is obtained from a fungus.

9. The polypeptide of claim 1 having sialidase activity that is recombinantly produced in a food grade host cell and which is a fungal sialidase having a molecular weight of less than 55 kDa as determined by SDS-PAGE.

10. An isolated polynucleotide comprising a nucleic acid sequence which encodes the polypeptide of claim 1.

11. An isolated nucleic acid construct comprising the polynucleotide of claim 10 operably linked to one or more control sequences that direct the production of the polypeptide in a suitable expression host.

12. A recombinant expression vector comprising the nucleic acid construct of claim 11.

13. An isolated recombinant host cell comprising the vector of claim 12.

14. A method for producing a sialidase polypeptide comprising cultivating a recombinant host cell according to claim 13 to produce a supernatant and/or cells comprising the polypeptide; and recovering the polypeptide from said supernatant or from said cells.

15. The polypeptide produced by the method of claim 14, which has a molecular weight of less than 55 kDa as determined by SDS-PAGE.

16. The polypeptide produced by the method of claim 14, which has a molecular weight of less than 50 kDa as calculated on basis of its amino acid sequence.

17. The polypeptide of claim 16 which has a molecular weight of less than 45 kDa as calculated on the basis of its amino acid sequence.

18. A method for producing a sialidase polypeptide comprising cultivating a host cell comprising a nucleic acid construct comprising a polynucleotide of claim 10 under conditions suitable for production of the encoded sialidase polypeptide and recovering the sialidase polypeptide from the host cell.

19. The polypeptide produced by the method of claim 18.

20. A method of preparing a food or a feed using a sialidase polypeptide according to claim 1 comprising adding the polypeptide to a food or a feed and incubating the food or feed comprising the added polypeptide for a time sufficient to permit the removal of sialic acid residues from proteins in the food or feed.

* * * * *

SEQUENCE LISTING

```
<160> NUMBER OF SEQ ID NOS: 5

<210> SEQ ID NO 1
<211> LENGTH: 2542
<212> TYPE: DNA
<213> ORGANISM: Penicillium chrysogenum

<400> SEQUENCE: 1
agctgaagaa tagatgaatt tctatgttgc gaataatagt agtttccaat actacaaatt      60
tggagagtca ttaagtacta aaatgtttgg atatccccac ctagcgtggg gattgggtca     120
gtgctatttg acccgatcgc gtcgcaaatg caacccgatc ggatcggagt ccggtcttcg     180
cggtcgtatt cagacatcta gcgggccat caatagcgcg tggtaacgca tgacactgcg     240
tggcgtcgca tgtctgattc agtggttcgc ttcagttctt caacgttgcg gtcaatgaga     300
ttgtggtaac gcagtcagca tacagatcct gtgaagctaa accagcagag ccagtgggac     360
cagtgggacc agtggatacc ttccactccc cagggtctgc attttccggg gaaaccgacg     420
taagccaagg aactcaaaat tggtatgtac tatctatcct ctaccgtca atacatacta      480
```

```
tgtgttattg gatttccctc tatcaaatcg aatagactgc atagattgca gtcctttcct    540
ttcgtcagat tatccagatt atccagatca gtcccgaaag tgaaactgaa tccaatcttc    600
gatataaata gctccttgtt cctccaaaaa aacaagagtc atcatctcag ttagctgttt    660
ccacacttcc tctttcactc aaaagcccgc ttttcaggt caattttagt ggactaactt     720
cacgatgcta tcttcattga tgtatttggc acgtgagtgc tccatcttgc gcgctatctc    780
cttatgtgcc atcctcgccg tggcaactcc tgcggcgagc gcaagcgtca cagcaaagca    840
cacgctggcc acaaatggaa aggggctgtt tccacagtac cgaattgttg ccttggcaag    900
tctgggaaat ggtgttctcc tggcctcata tgatgggcgc ccagatggag gagattcgcc    960
atccccaaat tcaattctac aacgacgcag tacggacggt gggaagactt ggggcaaccc   1020
aacatatatt gcgcgaggtc aaccagcgtc gtcgacactc aacagtacg gctttagtga    1080 cccaagctac gtggtcgact ccggtactgg aaaggtcttt aatttccatg tcttctcgaa   1140
gaaccaggga tttctcaata gcgaaattgg aaatgacgac accgacttaa acatagtcag   1200
cgctgaagtc tccgtttcga ctgatggagg acttagctgg accactgatc cagaccatga   1260
atcctctttg cctcccgttg catctgccga cgttggtgca ccgccactca ttacgaaagc   1320
aatcaagccc gtgggtagta cttccaacgg ggtagccaac gtcggtggaa ttactgggat   1380
gtttgcctca tccggagagg ggattcaact caaatacggc aaaacgccg ggcgcctggt    1440 tcaacaattc cttgggaaag tcatccaatc agacggttca aaggtctcgc aagcctacag   1500
tgtctacagt gacgacggtg gcgctatatg aagatgggg aaagtcattg gcactgggat    1560
ggatgagaac aaagttgtgg agctatcaaa cggcaacttg atgcttaact cacgcccgag   1620
cgatggtagc ggatatcgaa aggtggcaac ctcaaccgat ggtggtgaaa cttggtcaac   1680
accagcaagc gaaacccaac tccctgaccc aggaaataac ggagcaatta ccaggatgta   1740
tcctgatgcg gcacatggtt cggccaatgc caagatcctc ctgtttacca atgcaaacag   1800
taaaacaagc cgaagcaatg gtacaatccg ctattcctgt gacgacggaa agacctggtc   1860
ttctggcgca gtgttccagt ctggctcgat gtcctattcc actgtcaccg cactcggcga   1920
tgacaggttc ggaatatttt acgagggga tagcaacgac ctcgtctaca ttgaagtttc    1980
caaggatttt attggggttt cctgctgata aaactcccat tggcagtgtg ctctacttgg   2040
gaacttggtt tttacattgt acctaggtct atgtgtacat gtatgtacta cagcgtcatc   2100
tcaaatattc ttttgggaaa ggacctgaca atggcggcag catgatggat tttgtggctc   2160
ggccatttat tgacgatggc acacgatagc tatcgaactc actggtagct attgcgaatg   2220
ttcagtacag gtggcgttgg ttcctctagt cacgcctgga tgaaatcaga ccgttatagt   2280
gacaccttcc tatgacacta tattctgtat tgtgaaccca atatttccat ggtagtagtt   2340
tcaggtgaca gcaagggcaa aaattcttat tgctcaaaag taacattgca tgtagagatc   2400
ccatagtcaa ggtggcgttt gagagattta taggtggtaa aatcatgcta tttttaggct   2460
taggaacaat gctcgcaaga cgaacgaacg atgtagtagg ttggattaga gcccagtaag   2520
aatggaattc ctatcacaag ca                                            2542
```

<210> SEQ ID NO 2
<211> LENGTH: 1224
<212> TYPE: DNA
<213> ORGANISM: Penicillium chrysogenum
<220> FEATURE:
<221> NAME/KEY: CDS
<222> LOCATION: (1)..(1224)

```
<400> SEQUENCE: 2 atg cta tct tca ttg atg tat ttg gca cgt gag tgc tcc atc ttg cgc      48
Met Leu Ser Ser Leu Met Tyr Leu Ala Arg Glu Cys Ser Ile Leu Arg
 1               5                  10                  15 gct atc tcc tta tgt gcc atc ctc gcc gtg gca act cct gcg gcg agc      96
Ala Ile Ser Leu Cys Ala Ile Leu Ala Val Ala Thr Pro Ala Ala Ser
             20                  25                  30 gca agc gtc aca gca aag cac acg ctg gcc aca aat gga aag ggg ctg     144
Ala Ser Val Thr Ala Lys His Thr Leu Ala Thr Asn Gly Lys Gly Leu
         35                  40                  45 ttt cca cag tac cga att gtt gcc ttg gca agt ctg gga aat ggt gtt     192
Phe Pro Gln Tyr Arg Ile Val Ala Leu Ala Ser Leu Gly Asn Gly Val
     50                  55                  60 ctc ctg gcc tca tat gat ggg cgc cca gat gga gga gat tcg cca tcc     240
Leu Leu Ala Ser Tyr Asp Gly Arg Pro Asp Gly Gly Asp Ser Pro Ser
 65                  70                  75                  80 cca aat tca att cta caa cga cgc agt acg gac ggt ggg aag act tgg     288
Pro Asn Ser Ile Leu Gln Arg Arg Ser Thr Asp Gly Gly Lys Thr Trp
                 85                  90                  95 ggc aac cca aca tat att gcg cga ggt caa cca gcg tcg tcg aca ctc     336
Gly Asn Pro Thr Tyr Ile Ala Arg Gly Gln Pro Ala Ser Ser Thr Leu
            100                 105                 110 caa cag tac ggc ttt agt gac cca agc tac gtg gtc gac tcc ggt act     384
Gln Gln Tyr Gly Phe Ser Asp Pro Ser Tyr Val Val Asp Ser Gly Thr
        115                 120                 125 gga aag gtc ttt aat ttc cat gtc ttc tcg aag aac cag gga ttt ctc     432
Gly Lys Val Phe Asn Phe His Val Phe Ser Lys Asn Gln Gly Phe Leu
    130                 135                 140 aat agc gaa att gga aat gac gac acc gac tta aac ata gtc agc gct     480
Asn Ser Glu Ile Gly Asn Asp Asp Thr Asp Leu Asn Ile Val Ser Ala
145                 150                 155                 160 gaa gtc tcc gtt tcg act gat gga gga ctt agc tgg acc act gat cca     528
Glu Val Ser Val Ser Thr Asp Gly Gly Leu Ser Trp Thr Thr Asp Pro
                165                 170                 175 gac cat gaa tcc tct ttg cct ccc gtt gca tct gcc gac gtt gcc aac     576
Asp His Glu Ser Ser Leu Pro Pro Val Ala Ser Ala Asp Val Ala Asn
            180                 185                 190 gtc ggt gga att act ggg atg ttt gcc tca tcc gga gag ggg att caa     624
Val Gly Gly Ile Thr Gly Met Phe Ala Ser Ser Gly Glu Gly Ile Gln
        195                 200                 205 ctc aaa tac ggc aaa cac gcc ggg cgc ctg gtt caa caa ttc ctt ggg     672
Leu Lys Tyr Gly Lys His Ala Gly Arg Leu Val Gln Gln Phe Leu Gly
    210                 215                 220 aaa gtc atc caa tca gac ggt tca aag gtc tcg caa gcc tac agt gtc     720
Lys Val Ile Gln Ser Asp Gly Ser Lys Val Ser Gln Ala Tyr Ser Val
225                 230                 235                 240 tac agt gac gac ggt ggc gct ata tgg aag atg ggg aaa gtc att ggc     768
Tyr Ser Asp Asp Gly Gly Ala Ile Trp Lys Met Gly Lys Val Ile Gly
                245                 250                 255 act ggg atg gat gag aac aaa gtt gtg gag cta tca aac ggc aac ttg     816
Thr Gly Met Asp Glu Asn Lys Val Val Glu Leu Ser Asn Gly Asn Leu
            260                 265                 270 atg ctt aac tca cgc ccg agc gat ggt agc gga tat cga aag gtg gca     864
Met Leu Asn Ser Arg Pro Ser Asp Gly Ser Gly Tyr Arg Lys Val Ala
        275                 280                 285 acc tca acc gat ggt ggt gaa act tgg tca aca cca gca agc gaa acc     912
Thr Ser Thr Asp Gly Gly Glu Thr Trp Ser Thr Pro Ala Ser Glu Thr
    290                 295                 300 caa ctc cct gac cca gga aat aac gga gca att acc agg atg tat cct     960
Gln Leu Pro Asp Pro Gly Asn Asn Gly Ala Ile Thr Arg Met Tyr Pro
```

```
                    305                 310                 315                 320
gat gcg gca cat ggt tcg gcc aat gcc aag atc ctc ctg ttt acc aat              1008
Asp Ala Ala His Gly Ser Ala Asn Ala Lys Ile Leu Leu Phe Thr Asn
                325                 330                 335 gca aac agt aaa aca agc cga agc aat ggt aca atc cgc tat tcc tgt              1056
Ala Asn Ser Lys Thr Ser Arg Ser Asn Gly Thr Ile Arg Tyr Ser Cys
                340                 345                 350 gac gac gga aag acc tgg tct tct ggc gca gtg ttc cag tct ggc tcg              1104
Asp Asp Gly Lys Thr Trp Ser Ser Gly Ala Val Phe Gln Ser Gly Ser
                355                 360                 365 atg tcc tat tcc act gtc acc gca ctc ggc gat gac agg ttc gga ata              1152
Met Ser Tyr Ser Thr Val Thr Ala Leu Gly Asp Asp Arg Phe Gly Ile
        370                 375                 380 ttt tac gag ggg gat agc aac gac ctc gtc tac att gaa gtt tcc aag              1200
Phe Tyr Glu Gly Asp Ser Asn Asp Leu Val Tyr Ile Glu Val Ser Lys
385                 390                 395                 400 gat ttt att ggg gtt tcc tgc tga                                              1224
Asp Phe Ile Gly Val Ser Cys
                405

<210> SEQ ID NO 3
<211> LENGTH: 407
<212> TYPE: PRT
<213> ORGANISM: Penicillium chrysogenum

<400> SEQUENCE: 3

Met Leu Ser Ser Leu Met Tyr Leu Ala Arg Glu Cys Ser Ile Leu Arg
1               5                   10                  15

Ala Ile Ser Leu Cys Ala Ile Leu Ala Val Ala Thr Pro Ala Ala Ser
            20                  25                  30

Ala Ser Val Thr Ala Lys His Thr Leu Ala Thr Asn Gly Lys Gly Leu
        35                  40                  45

Phe Pro Gln Tyr Arg Ile Val Ala Leu Ala Ser Leu Gly Asn Gly Val
    50                  55                  60

Leu Leu Ala Ser Tyr Asp Gly Arg Pro Asp Gly Gly Asp Ser Pro Ser
65                  70                  75                  80

Pro Asn Ser Ile Leu Gln Arg Arg Ser Thr Asp Gly Lys Thr Trp
            85                  90                  95

Gly Asn Pro Thr Tyr Ile Ala Arg Gly Gln Pro Ala Ser Ser Thr Leu
            100                 105                 110

Gln Gln Tyr Gly Phe Ser Asp Pro Ser Tyr Val Val Asp Ser Gly Thr
        115                 120                 125

Gly Lys Val Phe Asn Phe His Val Phe Ser Lys Asn Gln Gly Phe Leu
    130                 135                 140

Asn Ser Glu Ile Gly Asn Asp Thr Asp Leu Asn Ile Val Ser Ala
145                 150                 155                 160

Glu Val Ser Val Ser Thr Asp Gly Gly Leu Ser Trp Thr Thr Asp Pro
                165                 170                 175

Asp His Glu Ser Ser Leu Pro Pro Val Ala Ser Ala Asp Val Ala Asn
            180                 185                 190

Val Gly Gly Ile Thr Gly Met Phe Ala Ser Ser Gly Glu Gly Ile Gln
        195                 200                 205

Leu Lys Tyr Gly Lys His Ala Gly Arg Leu Val Gln Gln Phe Leu Gly
    210                 215                 220

Lys Val Ile Gln Ser Asp Gly Ser Lys Val Ser Gln Ala Tyr Ser Val
225                 230                 235                 240

Tyr Ser Asp Asp Gly Gly Ala Ile Trp Lys Met Gly Lys Val Ile Gly
```

```
                        245                 250                 255
Thr Gly Met Asp Glu Asn Lys Val Val Glu Leu Ser Asn Gly Asn Leu
            260                 265                 270

Met Leu Asn Ser Arg Pro Ser Asp Gly Ser Gly Tyr Arg Lys Val Ala
            275                 280                 285

Thr Ser Thr Asp Gly Glu Thr Trp Ser Thr Pro Ala Ser Glu Thr
            290                 295                 300

Gln Leu Pro Asp Pro Gly Asn Asn Gly Ala Ile Thr Arg Met Tyr Pro
305                 310                 315                 320

Asp Ala Ala His Gly Ser Ala Asn Ala Lys Ile Leu Leu Phe Thr Asn
                325                 330                 335

Ala Asn Ser Lys Thr Ser Arg Ser Asn Gly Thr Ile Arg Tyr Ser Cys
            340                 345                 350

Asp Asp Gly Lys Thr Trp Ser Ser Gly Ala Val Phe Gln Ser Gly Ser
            355                 360                 365

Met Ser Tyr Ser Thr Val Thr Ala Leu Gly Asp Asp Arg Phe Gly Ile
            370                 375                 380

Phe Tyr Glu Gly Asp Ser Asn Asp Leu Val Tyr Ile Glu Val Ser Lys
385                 390                 395                 400

Asp Phe Ile Gly Val Ser Cys
                405

<210> SEQ ID NO 4
<211> LENGTH: 46
<212> TYPE: DNA
<213> ORGANISM: Artificial Sequence
<220> FEATURE:
<223> OTHER INFORMATION: synthetic primer

<400> SEQUENCE: 4
cccttaatta actcataggc atcatgctat cttcattgat gtattt            46

<210> SEQ ID NO 5
<211> LENGTH: 34
<212> TYPE: DNA
<213> ORGANISM: Artificial Sequence
<220> FEATURE:
<223> OTHER INFORMATION: synthetic primer

<400> SEQUENCE: 5
ttaggcgcgc cgtacataca tgtacacata gacc                         34
```